United States Patent
Wang

(10) Patent No.: US 10,278,586 B2
(45) Date of Patent: May 7, 2019

(54) COMPLEMENTARY COLOR FLASHING FOR MULTICHANNEL IMAGE PRESENTATION

(71) Applicant: LI-COR, Inc., Lincoln, NE (US)

(72) Inventor: Han-Wei Wang, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 0 days.

(21) Appl. No.: 15/630,776

(22) Filed: Jun. 22, 2017

(65) Prior Publication Data
US 2017/0367582 A1  Dec. 28, 2017

Related U.S. Application Data

(60) Provisional application No. 62/353,764, filed on Jun. 23, 2016, provisional application No. 62/425,967, filed on Nov. 23, 2016.

(51) Int. Cl.
*G02B 21/36* (2006.01)
*A61B 5/00* (2006.01)
(Continued)

(52) U.S. Cl.
CPC ............ *A61B 5/0071* (2013.01); *A61B 1/043* (2013.01); *A61B 1/0646* (2013.01);
(Continued)

(58) Field of Classification Search
CPC .......................... A61B 5/0777; G02B 21/367
(Continued)

(56) References Cited

U.S. PATENT DOCUMENTS

| 2,792,502 A | 5/1957 | O'Connor et al. |
| 5,103,338 A | 4/1992 | Crowley et al. |

(Continued)

FOREIGN PATENT DOCUMENTS

| CN | 101301192 | 11/2008 |
| CN | 102048525 | 5/2012 |

(Continued)

OTHER PUBLICATIONS

International Search Report dated Feb. 8, 2018, for PCT Appln No. PCT/US2017/062812, 4 pages.
(Continued)

*Primary Examiner* — Thomas J Lett
(74) *Attorney, Agent, or Firm* — Kilpatrick Townsend and Stockton LLP

(57) ABSTRACT

Methods are provided for the highlighting of features in composite images through the alternating of images having complementary colors. An image having a feature of interest is used to generate one or more pseudo color images. A series of a pseudo color images and one or more additional pseudo color or original color images are then alternately displayed so that the differently colored regions among the series of images are easily recognizable to an operator. The differently colored regions differ in having hues that are complementary to one another. The methods are particularly useful for the display of information using two or more imaging modalities and channels, such as is the case for some medical applications in which a natural-light image of pink or light-red tissue with deeper red or blue vasculature is overlaid with another functional image. In these cases, a feature present in the functional image can be more easily perceived when displayed in a composite overlay with an underlying image from another imaging modality or channel.

20 Claims, 12 Drawing Sheets

(51) Int. Cl.
  *A61B 1/04* (2006.01)
  *A61B 1/06* (2006.01)
  *G06T 11/00* (2006.01)
  *A61B 6/03* (2006.01)
  *A61B 6/00* (2006.01)
  *G01N 1/30* (2006.01)

(52) U.S. Cl.
  CPC ............ *A61B 5/0073* (2013.01); *G06T 11/00* (2013.01); *G06T 11/001* (2013.01); *A61B 6/032* (2013.01); *A61B 6/5247* (2013.01); *G01N 1/30* (2013.01); *G06K 2209/05* (2013.01); *G06T 2207/30004* (2013.01); *G06T 2210/41* (2013.01)

(58) Field of Classification Search
  USPC ........................................................ 345/629
  See application file for complete search history.

(56) References Cited

U.S. PATENT DOCUMENTS

| | | | |
|---|---|---|---|
| 5,224,141 | A | 6/1993 | Yassa et al. |
| 5,408,294 | A | 4/1995 | Lam |
| 5,812,265 | A | 9/1998 | Hoshiyama |
| 5,959,295 | A | 9/1999 | Braun |
| 6,165,170 | A | 12/2000 | Wynne et al. |
| 6,172,373 | B1 | 1/2001 | Hara et al. |
| 6,356,272 | B1 | 3/2002 | Matsumoto et al. |
| RE37,913 | E | 11/2002 | Nishi |
| 6,711,433 | B1 | 3/2004 | Geiger et al. |
| 7,218,393 | B2 | 5/2007 | Sharpe et al. |
| 7,286,232 | B2 | 10/2007 | Bouzid et al. |
| 7,453,456 | B2 | 11/2008 | Petrov et al. |
| 7,505,124 | B2 | 3/2009 | Kreckel et al. |
| 7,551,711 | B2 | 6/2009 | Sarment et al. |
| 7,715,523 | B2 | 5/2010 | Lafferty et al. |
| 7,929,743 | B2 | 4/2011 | Khorasani et al. |
| 8,115,918 | B2 | 2/2012 | Zavislan et al. |
| 8,220,415 | B2 | 7/2012 | Lamb et al. |
| 8,503,602 | B2 | 8/2013 | Lafferty et al. |
| 8,741,232 | B2 | 6/2014 | Baysal et al. |
| 8,754,384 | B1 | 6/2014 | Persoon et al. |
| 8,851,017 | B2 | 10/2014 | Lamb et al. |
| 8,892,192 | B2 | 11/2014 | Cuccia et al. |
| 9,053,563 | B2 | 6/2015 | Embrey et al. |
| 9,557,281 | B2 | 1/2017 | Yang et al. |
| 9,632,187 | B2 | 4/2017 | Poon et al. |
| 2003/0078477 | A1 | 4/2003 | Kang et al. |
| 2004/0101088 | A1 | 5/2004 | Sabol et al. |
| 2005/0046840 | A1 | 3/2005 | Kusuzawa et al. |
| 2005/0227374 | A1 | 10/2005 | Cunningham et al. |
| 2006/0072123 | A1 | 4/2006 | Wilson et al. |
| 2006/0250518 | A1 | 11/2006 | Nilson et al. |
| 2006/0253035 | A1 | 11/2006 | Stern |
| 2007/0121099 | A1 | 5/2007 | Matsumoto et al. |
| 2007/0276184 | A1 | 11/2007 | Okawa |
| 2008/0077019 | A1 | 3/2008 | Xiao et al. |
| 2008/0297890 | A1 | 12/2008 | Natori et al. |
| 2008/0312540 | A1 | 12/2008 | Ntziachristos |
| 2009/0011386 | A1 | 1/2009 | Eiff et al. |
| 2009/0018451 | A1 | 1/2009 | Bai et al. |
| 2009/0032731 | A1 | 2/2009 | Kimura et al. |
| 2009/0129543 | A1 | 5/2009 | Le Gros et al. |
| 2009/0192358 | A1 | 7/2009 | Jaffer et al. |
| 2009/0208072 | A1 | 8/2009 | Seibel et al. |
| 2009/0234225 | A1 | 9/2009 | Martin et al. |
| 2009/0250631 | A1 | 10/2009 | Feke et al. |
| 2010/0309548 | A1 | 12/2010 | Power |
| 2011/0116694 | A1 | 5/2011 | Gareau et al. |
| 2011/0135190 | A1 | 6/2011 | Maad |
| 2011/0229023 | A1 | 9/2011 | Jones et al. |
| 2012/0049087 | A1 | 3/2012 | Choi et al. |
| 2012/0049088 | A1 | 3/2012 | Klose |
| 2012/0065518 | A1 | 3/2012 | Mangoubi et al. |
| 2012/0105600 | A1 | 5/2012 | Meyer et al. |
| 2012/0182411 | A1 | 7/2012 | Nakatsuka et al. |
| 2012/0194663 | A1 | 8/2012 | Haisch et al. |
| 2012/0206577 | A1 | 8/2012 | Guckenberger et al. |
| 2012/0302880 | A1 | 11/2012 | Tian et al. |
| 2012/0312957 | A1 | 12/2012 | Loney et al. |
| 2013/0027516 | A1 | 1/2013 | Hart et al. |
| 2013/0135081 | A1 | 5/2013 | McCloskey et al. |
| 2014/0125790 | A1 | 5/2014 | Mackie et al. |
| 2014/0140594 | A1 | 5/2014 | Mahadevan-Jansen et al. |
| 2014/0163388 | A1 | 6/2014 | Sasayama et al. |
| 2014/0276008 | A1 | 9/2014 | Steinbach et al. |
| 2014/0294247 | A1 | 10/2014 | Sirault et al. |
| 2014/0346359 | A1 | 11/2014 | Holliday |
| 2014/0349337 | A1 | 11/2014 | Dasari et al. |
| 2014/0378843 | A1 | 12/2014 | Valdes et al. |
| 2015/0000410 | A1 | 1/2015 | Grimard et al. |
| 2015/0022824 | A1 | 1/2015 | Babayoff |
| 2015/0062153 | A1 | 3/2015 | Mihalca et al. |
| 2015/0073213 | A1 | 3/2015 | Khait et al. |
| 2015/0098126 | A1 | 4/2015 | Keller et al. |
| 2015/0105283 | A1 | 4/2015 | Hollman-Hewgley et al. |
| 2015/0359413 | A1 | 12/2015 | Rainis |
| 2016/0187199 | A1 | 6/2016 | Brunk et al. |
| 2016/0245753 | A1 | 8/2016 | Wang |
| 2016/0377545 | A1 | 12/2016 | Wang |
| 2017/0059487 | A1 | 3/2017 | Wang |
| 2017/0309063 | A1 | 10/2017 | Wang |
| 2017/0336706 | A1 | 11/2017 | Wang |
| 2018/0140197 | A1 | 5/2018 | Wang et al. |

FOREIGN PATENT DOCUMENTS

| | | |
|---|---|---|
| CN | 103082997 | 10/2015 |
| DE | 102011104216 | 12/2012 |
| EP | 2455891 | 5/2012 |
| GB | 2514125 | 11/2014 |
| KR | 20130096910 | 9/2013 |
| WO | 2006113908 | 10/2006 |
| WO | 2007030424 | 3/2007 |
| WO | 2009115061 | 9/2009 |
| WO | 2013166497 | 11/2013 |
| WO | 2014094142 | 6/2014 |
| WO | 2016014252 | 1/2016 |
| WO | 2016073569 | 5/2016 |
| WO | 2016100214 | 6/2016 |
| WO | 2016137899 | 9/2016 |
| WO | 2016210340 | 12/2016 |
| WO | 2017184940 | 10/2017 |
| WO | 2017200801 | 11/2017 |
| WO | 2017223378 | 12/2017 |
| WO | 2018098162 | 5/2018 |

OTHER PUBLICATIONS

Lee et al., "Fusion of coregistered cross-modality images using a temporally alternating display method", Medical & Biological Engineering & Computing, Springer, vol. 38, No. 2, Mar. 1, 2000, pp. 127-132.
International Search Report and Written Opinion dated Sep. 22, 2017 for PCT/US2017/028769, 19 pages.
International Search Report and Written Opinion dated Sep. 19, 2017 for PCT/US2017/031740, 25 pages.
International Search Report and Written Opinion dated Sep. 22, 2017 for PCT/US2017/038860, 13 pages.
"Arctec Eva Fast Handheld 3D Scanner for Professionals," http://www.artec3d.com/hardware/artec-evat/, retrieved from the internet Apr. 19, 2016, 6 pages.
"Optical Scatter Imaging System for Surgical Specimen Margin Assessment During Breast Conserving Surgery", Project Information NIH Research Portfolio Online Reporting Tools, Project No. 1R01CA192803-01, 2 pages.
Bioptics Inc., "BioVision Digital Specimen Radiography (DSR) System", Premarket Notification 510(k) Summary, prepared May 2009, 8 pages.
Fang et al., "Combined Optical and X-ray Tomosynthesis Breast Imaging", Radiology, vol. 258, No. 1, Jan. 2011, pp. 89-97.

(56) References Cited

OTHER PUBLICATIONS

Faxitron Bioptics LLC, "BioVision Surgical Specimen Radiography System", http://www.faxitron.com/medical/products/biovision.html, retrieved from the internet Apr. 26, 2016, 2 pages.
Faxitron Bioptics LLC, "Path Vision", http://www.faxitron.com/medical/products/pathvision.html, retrieved from the internet Apr. 26, 2016, 2 pages.
Lamberts et al., "Tumor-specific uptake of fluorescent bevacizumab-IRDye800CW microdosing in patients with primary breast cancer: a phase I feasibility study", Clinical Cancer Research, Personalized Medicine and Imaging, American Association for Cancer Research, 2016, 41 pages.
Perkin Elmer, "Every Cancer Tells a Story If You Have the Tools to Read It", http://go.perkinelmer.com/webmail/32222/179460051/9c4865b118d5295e96e973a5b6c28bad, 2 pages.
Tomowave Laboratories, "Imaging Modules", retrieved from the internet http://www.tomowave.com/imagingmodules.html, 1 page.
Wu et al., "Rotational imaging optical coherence tomography for full-body mouse embryonic imaging", Journal of Biomedical Optics, vol. 21, No. 2, Feb. 2016, pp. 026002-1-026002-9.
U.S. Appl. No. 15/352,427, "Non-Final Office Action", dated Sep. 4, 2018, 9 pages.
U.S. Appl. No. 15/352,427, "Notice of Allowance", dated Nov. 21, 2018, 6 pages.
EP application No. EP16756129.9, "Partial European Search Report", dated Oct. 29, 2018, 17 pages.
PCT application No. PCT/US2017/028769, "International Preliminary Report on Patentability", dated Nov. 1, 2018, 13 pages.
International Search Report for PCT/US2018/027978, dated Jul. 12, 2018, 13 pages.
Sturm et al., "CopyMe3D: Scanning and Printing Persons in 3D", Medical Image Computing and Computer-Assisted Intervention—Miccai 2015: 18th International Conference, Munich, Germany, Sep. 3, 2013, pp. 405-414.
U.S. Appl. No. 15/352,427, "Notice of Allowance," dated Nov. 21, 2018, 6 pages (not attached).
EP16756129.9, "Partial European Search Report," dated Oct. 29, 2018, 17 pages.
Badawi et al., Real-Time Tissue Assessment During Surgical Procedures, UC David Office of Research, Tech ID: 24307.
Orpheus Medical, Clinical Video Management and Visible Light Documentation, Slideshow dated Feb. 3, 2016. The Examiner's attention is directed to slide 11.
U.S. Appl. No. 15/192,771, "Final Office Action," dated Jan. 8, 2019, 10 pages (no copy provided).
EP16756129.9, "Supplementary European Search Report," dated Jan. 29, 2019, 14 pages.
EP16815434.2, "Partial Supplementary European Search Report," dated Jan. 29, 2019, 16 pages.
PCT/US2017/038860, "International Preliminary Report on Patentability," dated Jan. 3, 2019, 8 pages (no copy provided).

COMPLEMENTARY COLOR FLASHING FOR MULTICHANNEL IMAGE PRESENTATION

CROSS-REFERENCES TO RELATED APPLICATIONS

This application claims the benefit of U.S. Provisional Patent Application No. 62/353,764, filed Jun. 23, 2016, and U.S. Provisional Patent Application No. 62/425,967, filed Nov. 23, 2016, each of which is incorporated by reference in its entirety herein for all purposes.

BACKGROUND

In modern biological and medical imaging technologies, multiple imaging channels or multiple imaging modalities are frequently used together to offer complementary or additional information. For instance, a fluorescence channel can be used together with a white light channel to identify fluorescence signal from biological or molecular targets on top of the anatomical features presented in the white light image. As another example, a functional image of radioactive agents can be shown on a tomographic anatomical image, such as that produced by computed tomography (CT) or magnetic resonance imaging (Mill), to help localize diseases in a subject (U.S. Pat. No. 8,538,504; Yoshino et al. (2015) J. Radiation Res., 56:588-593).

Frequently, a pseudo-color or a color map is selected for one image channel so that it can better provide additional information when visualized on top of one or more other image channels. This concept has been used in many different research areas, such as those of clinical translational studies, as well as in medical care areas when applying a variety of imaging technologies.

Very often, real-time visualization is critical to enabling rapid recognition and understanding of imaging information presented in the format of a still frame, an animation, an augmented view, or a video. This can be particularly important when timely decision-making is required in response to accurate perception of a scenario via one or more imaging modalities. With this in mind, developments have been made in not only optical collection and sensing electronics for fluorescence, but in the uses of color maps and pseudo colors as applied to overlaid images (Elliot et al. (2015) Biomedical Optics Express, 6:3765-3782). In most of these scenarios, a reflective or white light image is as an underlying image that is presented together with one or more superimposed or co-localized fluorescence results (U.S. Pat. Nos. 7,330,749; 8,131,476).

In visualizing overlaid signals on a display, different perception factors, such as those of color selection, lightness, and transparency/alpha, can be adjusted. As human eyes are most sensitive to lightness, a fusion image can use a constant color map with changing lightness to indicate the most important scalar value, such as imaging agent concentration, targeted molecule concentration, grading, depth, severity, etc. Alternatively, a presentation scheme using a lookup table of different color saturations or color hues can be used to indicate scalar values. Information can also be presented by relying on differing transparency/alpha values at constant lightness and hue.

However, with these image fusion presentation schemes, it is often difficult for an operator to see the pseudo colors against the background of an underlying image. This is particularly the case when the underlying image channel is a true-color reflective light image or a bright tomographic section of a tissue or an object, as these are frequently characterized by large variations in color or brightness. For example, an underlying image can be a natural-light image of pink or light-red tissue with deeper red or blue vasculature.

To assist in visualizing signal with minimal interference, it has been proposed to allow a user to manually switch off one or more image channels, such as a reflective light channel, in order to better recognize the signal associated with another channel before turning the off channels back on. Alternatively, a component of a composite picture can be sinusoidally pulsed relative to the other elements of the composite picture (Glatz et al. (2014) J. Biomedical Optics, 19:040501). In this approach, the average background hue is calculated in order to guide the selection of the pulsed color. Yet these techniques can pose problems of decreased time efficiency, reduced ease-of-use, or lower effectiveness, particularly when presenting weak signals.

BRIEF SUMMARY

In general, provided herein are methods for displaying visual information by flashing complementary colors representing information of interest within an overlay of static images or video frames. An original color of an image is replaced with one or more complementary colors. These complementary colors are then flashed in a composite image that can comprise multiple images depicting the same subject. The complementary nature of the colors and the dynamic presentation of the colors through flashing can improve the perception of signal areas within the images or frames. This in turn can maximize the transfer of visual information to an operator and can minimize interpretive errors in acquiring data from the presented images.

One provided method for displaying images comprises receiving a first image. The first image comprises an original color and represent a view from a viewpoint. The method further comprises acquiring a second image. The second image represents a view from the viewpoint. The method further comprises generating a third image by replacing the original color of the first image with a first false color having a first hue. The method further comprises producing a fourth image by replacing the original color of the first image with a second false color having a second hue. The second hue is complementary to the first hue. The method further comprises rendering a fifth image by overlaying the third image and the second image. The method further comprises constructing a sixth image by overlaying the fourth image and the second image. The method further comprises alternately displaying the fifth and sixth images.

In some embodiments, the first image has a minimum first image color value and a maximum first image color value. In some embodiments, the first false color and the second false color have a false color value that is within the range between the minimum and maximum first image color values. In some embodiments, the first false color is black and the second false color is white.

In some embodiments, the alternately displaying is performed at a frequency. In some embodiments, the frequency of the alternately displaying is between 0.1 Hz and 25 Hz.

In some embodiments, the first and second images each represent views of a biological sample. In some embodiments, the biological sample is an in vivo sample. In some embodiments, the biological sample is an ex vivo sample. In some embodiments, the biological sample is from a mammalian subject. In some embodiments, the biological sample comprises a tumor.

In some embodiments, the first image is a fluorescence image, an X-ray image, a positron emission tomography (PET) image, a photon emission computed tomography (SPECT) image, a magnetic resonance imaging (MRI) image, a nuclear magnetic resonance (NMR) image, an ultrasound image, an autoradiography image, an immunohistochemistry image, or a microscopy image. In some embodiments, the second image is a reflected light image or a tomography image.

In some embodiments, the first image is recorded using a first camera or imager. In some embodiments, the second image is recorder using a second camera or imager. In some embodiments, the first camera or imager is the second camera or imager.

In some embodiments, the method further comprises accepting operator input selecting the frequency of the alternately displaying. In some embodiments, the method further comprises accepting operator input selecting the viewpoint.

Also provided is a method of displaying images, wherein the method comprises receiving a first image. The first image comprises an original color and represents a view from a viewpoint. The method further comprises generating a second image by replacing the original color of the first image with a first false color having a first hue. The method further comprises producing a third image by replacing the original color of the first image with a second false color having a second hue. The second hue is complementary to the first hue. The method further comprises alternately displaying the second and third images.

In some embodiments, the first image has a minimum first image color value and a maximum first image color value. In some embodiments, the first false color and the second false color have a false color value that is within the range between the minimum and maximum first image color values. In some embodiments, the first false color is black and the second false color is white.

In some embodiments, the alternately displaying is performed at a frequency. In some embodiments, the frequency of the alternately displaying is between 0.1 Hz and 25 Hz.

In some embodiments, the first image represents a view of a biological sample. In some embodiments, the biological sample is an in vivo sample. In some embodiments, the biological sample is an ex vivo sample. In some embodiments, the biological sample is from a mammalian subject. In some embodiments, the biological sample comprises a tumor.

In some embodiments, the first image is a reflected light image, a fluorescence image, an X-ray image, a PET image, a SPECT image, an MM image, an NMR image, an ultrasound image, an autoradiography image, an immunohistochemistry image, or a microscopy image.

In some embodiments, the method further comprises accepting operator input selecting the frequency of the alternately displaying. In some embodiments, the method further comprises accepting operator input selecting the viewpoint.

Also provided is a method of displaying images, the method comprising receiving a first image. The first image comprises an original color having a first hue and represents a view from a viewpoint. The method further comprises generating a second image by replacing the original color of the first image with a false color having a second hue. The second hue is complementary to the first hue. The method further comprises alternately displaying the first and second images.

In some embodiments, the first image has a minimum first image color value and a maximum first image color value. In some embodiments, the false color has a false color value that is within the range between the minimum and maximum first image color values. In some embodiments, one of the original color or the false color is black, and the other of the original color or the false color is white.

In some embodiments, the alternately displaying is performed at a frequency. In some embodiments, the frequency of the alternately displaying is between 0.1 Hz and 25 Hz.

In some embodiments, the first image represents a view of a biological sample. In some embodiments, the biological sample is an in vivo sample. In some embodiments, the biological sample is an ex vivo sample. In some embodiment, the biological sample is from a mammalian subject. In some embodiments, the biological sample comprises a tumor.

In some embodiments, the first image is a reflected light image, a fluorescence image, an X-ray image, a PET image, a SPECT image, an MM image, an NMR image, an ultrasound image, an autoradiography image, an immunohistochemistry image, or a microscopy image.

In some embodiments, the method further comprises accepting operator input selecting the frequency of the alternately displaying. In some embodiments, the method further comprises accepting operator input selecting the viewpoint.

Also provided is a method of displaying images, the method comprising receiving a first image. The first image comprises an original color having a first hue and represents a view from a viewpoint. The method further comprises acquiring a second image representing a view from the viewpoint. The method further comprises generating a third image by replacing the original color of the first image with a false color having a second hue. The second hue is complementary to the first hue. The method further comprises rendering a fourth image by overlaying the third image and the second image. The method further comprises constructing a fifth image by overlaying the first image and the second image. The method further comprises alternately displaying the fourth and fifth images.

In some embodiments, the first image has a minimum first image color value and a maximum first image color value. In some embodiment, the false color has a false color value that is within the range between the minimum and maximum first image color values. In some embodiments, one of the original color or the false color is black, and the other of the original color or the false color is white.

In some embodiments, the alternately displaying is performed at a frequency. In some embodiments, the frequency of the alternately displaying is between 0.1 Hz and 25 Hz.

In some embodiments, the first and second images each represent views of a biological sample. In some embodiments, the biological sample is an in vivo sample. In some embodiments, the biological sample is an ex vivo sample. In some embodiments, the biological sample is from a mammalian subject. In some embodiments, the biological sample comprises a tumor.

In some embodiments, the first image is a fluorescence image, an X-ray image, a PET image, a SPECT image, an MM image, an NMR image, an ultrasound image, an autoradiography image, an immunohistochemistry image, or a microscopy image. In some embodiments, the second image is a reflected light image or a tomography image.

In some embodiments, the first image is recorded using a first camera or imager. In some embodiments, the second image is recorder using a second camera or imager. In some embodiments, the first camera or imager is the second camera or imager.

In some embodiments, the method further comprises accepting operator input selecting the frequency of the alternately displaying. In some embodiments, the method further comprises accepting operator input selecting the viewpoint.

DETAILED DESCRIPTION

Embodiments of the present invention relate in part to the use of complementary color flashing to display information in composite images. The methods disclosed can be used to enhance visual perception of superimposed data by applying complementary colors and dynamic image changes. Although not being bound to any particular theory, it is believed that a reduction of the visual sensitivity of an operator is minimized by phototransduction refreshment of human photoreceptors through the viewing of complementary colors. Also, the use of dynamic stimulations with flicking or flashing frequencies takes advantage of the ability of the human visual system to better recognize signals that are dynamic in nature.

Using the provided methods, overlaid pseudo-color images can be quickly and effectively visualized and perceived to achieve the goals of maximizing information transfer and minimizing interpretive errors. The perception of signal distribution in composite images can be obtained in real-time and can be applied to multimodal or multichannel image data.

While a co-localized or superimposed static image can provide for an immediate review of overlaid signals among multiple different channels, very often the bright signal of one channel can reduce the perceived contrast with one or more other pseudo-colored channels. This can be true, for example, for bright signals associate with reflective true-color images, computed tomography (CT) contrast images, or X-ray images. The use of dynamic switching of one or more pseudo colors, typically selected to be complementary in color, on a static image or video can enhance this perceived contrast.

The methods of superimposing a complementary pseudo-colored image on top of an underlying image can be applied, for example, to medical image overlays. These overlay or composite images can incorporate information obtained from, for example, microscopy, spectral imaging, tomography, and clinical imaging. Imaging modalities can include X-ray, magnetic resonance imaging (MRI), positron emission tomography (PET), single-photon emission computed tomography (SPECT), and ultrasound. The needs of a clinician for such overlay visualization could include pre-operative information, intra-operative and image-guided content, diagnoses and analyses, planning and management, and post-operative verification or post-resection assessment.

Figure 1:
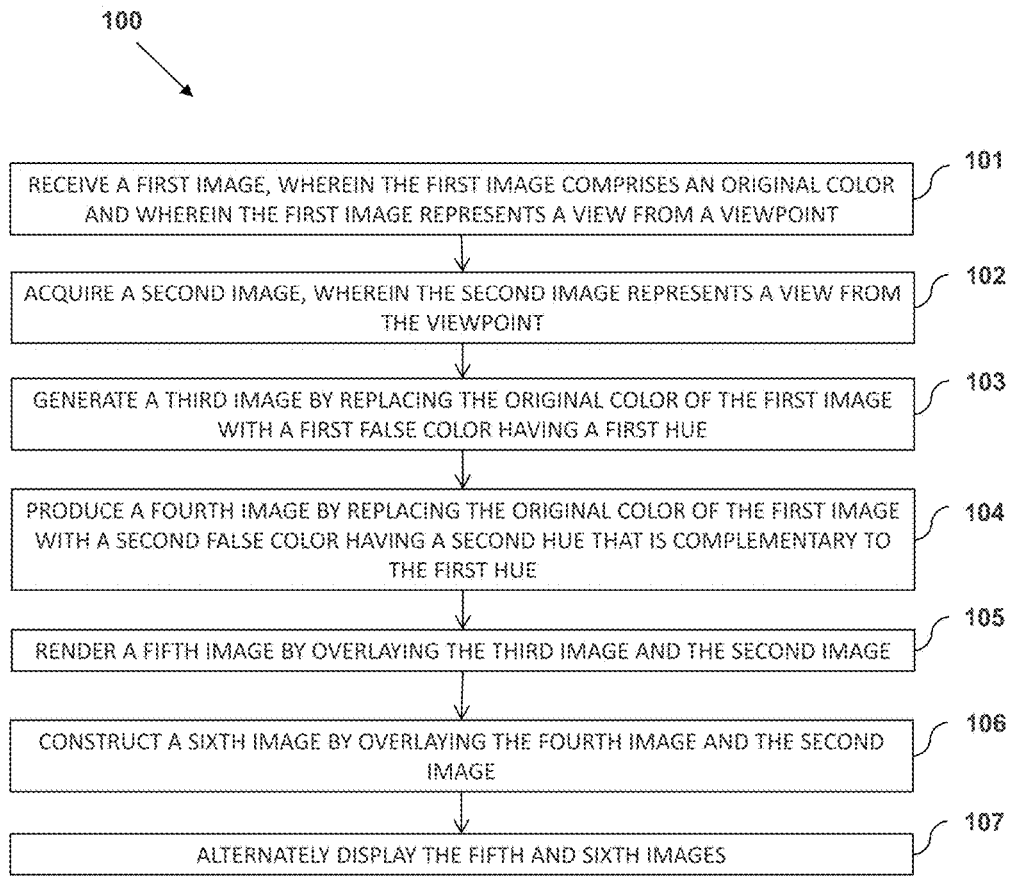
FIG. 1 is a flowchart of a process for alternately displaying two false color images derived from a first imaging channel, each false color image overlaid on an image from a second imaging channel.

FIG. 1 presents a flowchart of a process 100 for alternately displaying two false color images derived from a first imaging channel, each false color image overlaid on an image from a second imaging channel. In operation 101, a first image is received, wherein the first image comprises an original color and wherein the first image represents a view from a viewpoint. In operation 102, a second image is acquired, wherein the second image represents a view from the viewpoint. In operation 103, a third image is generated by replacing the original color of the first image with a first false color having a first hue. In operation 104, a fourth image is produced by replacing the original color of the first image with a second false color having a second hue that is complementary to the first hue. In operation 105, a fifth image is rendered by overlaying the third image and the second image. In operation 106, a sixth image is constructed by overlaying the fourth image and the second image. In operation 107, the fifth and sixth images are alternately displayed.

Figure 2:
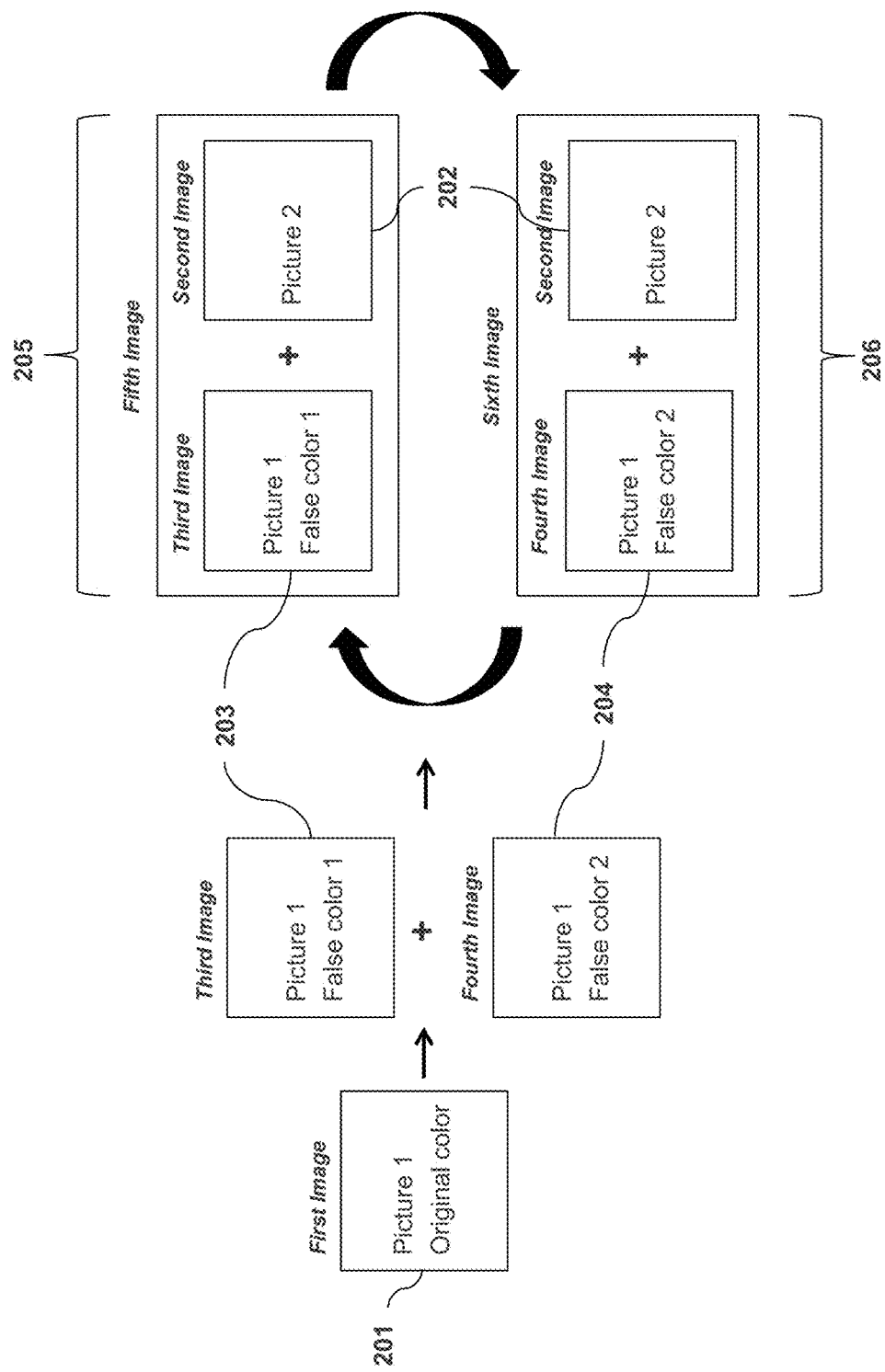
FIG. 2 is a schematic overview of an embodiment in accordance with the process of FIG. 1.

FIG. 2 provides a schematic overview of one embodiment in accordance with the process of FIG. 1. Shown are a first image 201 and a second image 202. A third image 203 and a fourth image 204 are each generated or produced from the first image 201 by replacing an original color of the first image with a false color. The false color of the third image 203 has a first hue, and the false color of the fourth image 204 has a second hue. The second hue is complementary to the first hue. A fifth image 205 is rendered by overlaying the third image 203 and the second image 202. A sixth image 206 is constructed by overlaying the fourth image 204 and the second image 202. The fifth image 205 and the sixth image 206 are then alternately displayed.

Figure 3:
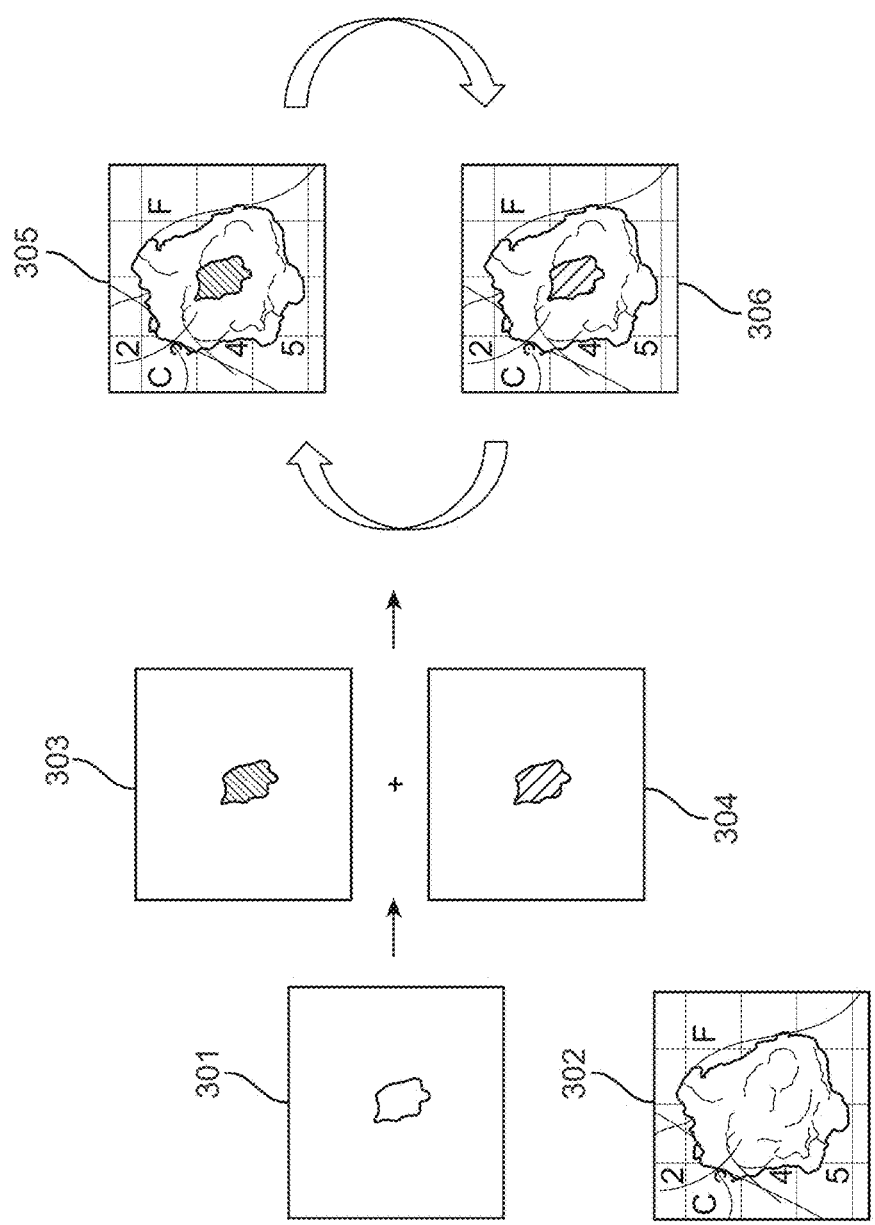
FIG. 3 is an illustration of an embodiment in accordance with the process of FIG. 1 and the schematic overview of FIG. 2.

FIG. 3 illustrates one embodiment in accordance with the process of FIG. 1 and the schematic overview of FIG. 2 as an example. Shown is a first image 301, which is a fluorescence image representing a biological sample as recorded using a fluorescence imaging channel or modality from a viewpoint. A second image 302 is a true color image representing the biological sample as recorded using a reflected light channel or modality from the same viewpoint. The original white color of the first image 301 is replaced by a false red color to generate a third image 303. The original white color of the first image 301 is replaced by a false green color to produce a fourth image 304. A fifth image 305 is rendered by overlaying the third image 303 and the second image 302. A sixth image 306 is constructed by overlaying the fourth image 304 and the second image 302. The fifth image 305 and the sixth image 306 are then alternately displayed. The complementarity of the red and green hues originating from the third 303 and fourth 304 images, as well as the dynamic presentation of the composite fifth 305 and sixth 306 images, allow a user to better discern the features of the original fluorescence image 301 when viewed simultaneously with the reflected light image 302. This can be particularly important in scenarios in which appreciating the location, shape, and edges of the fluorescent feature relative to positions on the biological sample is important.

The first image (201, 301) can be any visual representation having a feature of interest. In some embodiments, as in FIG. 3, the first image 301 is a fluorescence image of a biological sample. The first image can be a composite image of two or more imaging modalities, of two or more subjects and/or of two or more viewpoints. The first image can comprise information recorded of a physical object or scene. For example, the first image can be a photographic or tomographic image recorded using one or more imaging modalities. The first image can be a representation of a physical or abstract object or scene. For example, the first image can be of an illustration, a sketch, a computer-generated model, or a painting. The first image can be a static image or can be a frame of a video.

The first image (201, 301) can comprise any imaging modalities. In some embodiments, as in FIG. 3, the first image 301 comprises a fluorescence imaging modality. The first image can comprise an imaging modality of reflected light, X-ray, computerized tomography (CT), MRI, PET, SPECT, or ultrasound. In some embodiments, the first image comprises a single imaging modality. In some embodiments, the first image comprises two or more imaging modalities.

The first image (201, 301) can be received from any source. In some embodiments, the first image is retrieved from a computer memory system. In some embodiments, the first image is transmitted from a source that can be local or remote relative to the location of the image processing of the disclosed methods. In some embodiments, the first image is input, entered, or submitted by an operator. In some embodiments, the first image is recorded using a camera or imager for use with one of the disclosed method. In some embodiments, the first image is recorded using a camera or imager and is stored using a computer memory system prior to its being retrieved or transmitted for use with one of the disclosed methods.

One or more cameras or imagers can be used to record the first image (201, 301). The camera or imager can be configured to capture still images or video or movie images. The camera or imager can be configured to have any functional lens assembly, focal length, and exposure control sufficient to record the first image. The camera or imager can record the first image using a plate or film. The camera or imager can record the first image using an electronic image sensor. The camera or imager can comprise a charged coupled device (CCD) and/or a complementary metal-oxide-semiconductor (CMOS) sensor.

The first image (201, 301) comprises one or more original colors. In some embodiments, as in FIG. 3, the first image is a monochromatic image. In some embodiments, the first image comprises two or more colors. The reference to the one or more colors as being original colors is merely to specify that the colors are original to the first image, and not necessarily original to the subject of the first image. For example, electromagnetic radiation emitted or reflected by a subject at wavelengths outside of the spectrum visible to human perception can be represented by alternative visible wavelengths in a first image. In this example, the alternative wavelengths, while not original to the subject, are original to the first image representation of the subject, and are referred to herein as original colors.

As another example, a first image (201, 301) may represent data or information not associated with a color of a physical subject. This can be the case in representing, for example, data related to values for temperatures, pressures, concentrations, or any other non-visual parameter. In these cases, a first image can use a color scheme in which one or more colors are used to represent one or more different values or ranges of values for the non-visual parameters. In these examples, the representative colors are not original to a physical subject, but are original to the first image, and are referred to herein as original colors.

As a third example, a subject can emit or reflect electromagnetic radiation at visible wavelengths while a first image (201, 301) of the subject represents these visible colors with alternate colors. This can be the case, for example, when small differences between one or more colors emitted or reflected by the subject are exaggerated through the selection of an alternate color scheme. This can also be the case when the true colors reflected or emitted by a subject are difficult for at least some users to perceive. This can be the case, for example, with a population of users having one or more types of color blindness. In these examples, the alternative colors, while not original to the subject, are original to the first image representation of the subject, and are referred to herein as original colors.

The first image (201, 301) can be a view of a subject representative from a particular viewpoint. The view can be from any distance or angle relative to the subject. In some embodiments, the viewpoint is as least partially determined by the position of a camera or imager used to capture, record, store, or transmit the first image. In some embodiments, image manipulation is used such that the view is from a viewpoint other than the actual position of a camera or imager. Zooming, panning, or rotating functionalities can be used to alter the first image so that it represents a view from a different viewpoint in space. This different view can be the result of repositioning the camera or imager. The different view can be the result of selecting a different set of information that has been previously captured, recorded, stored, or transmitted while the camera or imager was in a different position. The different view can be the result of computer processing, such as with interpolation or extrapolation algorithms, to simulate a different position of the camera or imager.

The subject can be a biological sample. In some embodiments, the biological sample is one or more organisms. The biological subject can be one or more microscopic organisms. The biological sample can be a plant. The biological sample can be an animal. The biological sample can be a mammal. The biological sample can be a human. In some embodiments, the biological sample is a tissue, organ, or other subsection of an organism.

The biological sample can be an in vivo sample that is part or all of one or more living organisms. The biological sample can be an individual living microorganism. The biological sample can be a community of two or more living microorganisms. The biological sample can a living plant or animal. The biological sample can be a living mammal. The biological sample can be a living human. The biological sample can be a tissue, organ, or other subsection of a living human. In some embodiments, the biological sample is a region of an animal or human undergoing a surgical or other medical operation or analysis.

The biological sample can be an ex vivo sample of a tissue, organ, or other subsection removed from a plant or animal. The biological sample can be a tissue, organ, or other subsection removed from a mammal. The biological sample can be a tissue, organ, or other subsection removed from a human. In some embodiments, the biological sample is a resected human tissue sample. In some embodiments, the biological sample is a biopsy sample extracted from a human.

The biological sample can be of a mammalian subject. The mammalian subject can be, for example, rodent, canine, feline, equine, ovine, porcine, or a primate. The mammalian subject can be human.

The subject can be a patient suffering from a disease. In some embodiments, the subject is a cancer patient. In certain aspects, the biological sample comprises a tumor, such as tumor tissue or cells. In certain aspects, the biological sample comprises a peripheral biopsy of a tissue sample previously removed. In another aspect, the biological sample is tumor tissue such as a breast core biopsy. The biological sample size can be as small as a tissue slice.

The second image (202, 302) can be any visual representation from the same one or more viewpoints as that of the first image. In some embodiments, as in FIG. 3, the second image 302 is a reflected light image of a biological sample. The second image can be a composite image of two or more imaging modalities, of two or more subjects and/or of two or more viewpoints. The second image can comprise information recorded of a physical object or scene. For example, the second image can be a photographic or tomographic image recorded using one or more imaging modalities. The second image can be a representation of a physical or abstract object or scene. For example, the second image can be of an illustration, a sketch, a computer-generated model, or a painting. The second image can be a static image or can be a frame of a video.

The second image (202, 302) can comprise any imaging modalities. In some embodiments, as in FIG. 3, the second image 302 comprises a reflected light imaging modality. The second image can comprise an imaging modality of fluorescence, X-ray, CT, MRI, PET, SPECT, or ultrasound. In some embodiments, the second image comprises a single imaging modality. In some embodiments, the second image comprises two or more imaging modalities.

The second image (202, 302) can be received from any source. In some embodiments, the second image is retrieved from a computer memory system. In some embodiments, the second image is transmitted from a source that can be local or remote relative to the location of the image processing of the disclosed methods. In some embodiments, the second image is input, entered, or submitted by an operator. In some embodiments, the second image is recorded using a camera or imager for use with one of the disclosed method. In some embodiments, the second image is recorded using a camera or imager and is stored using a computer memory system prior to its being retrieved or transmitted for use with one of the disclosed methods.

One or more cameras or imagers can be used to record the second image (202, 302). The camera or imager can be configured to capture still images or video or movie images. The camera or imager can be configured to have any functional lens assembly, focal length, and exposure control sufficient to record the second image. The camera or imager can record the second image using a plate or film. The camera or imager can record the second image using an electronic image sensor. The camera or imager can comprise a charged coupled device (CCD) and/or a complementary metal-oxide-semiconductor (CMOS) sensor. In some embodiments, the same camera or imager is used to record or capture both the first (201, 301) and second image. In some embodiments, a first camera or imager is used to record or capture the first image, and a second camera or imager is used to record or capture the second image.

The third image (203, 303) is generated from the first image (201, 301) by replacing one or more selected original colors from the first image with one or more false colors. In some embodiments, one original color from the first image is replaced with one false color in generating the third image. In some embodiments, two or more original colors from the first image are each replaced with one false color in generating the third image.

The generation of the third image (203, 303) can comprise the use of a computer system and a computation algorithm to replace the one or more selected original colors from the first image (201, 301). In some embodiments, the third image is stored subsequent to its generation and prior to its use in rendering the fifth image (205, 305). In some embodiments, the third image is used to render the fifth image directly after the generation of the third image.

The false color used to replace the selected original color of the first image (201, 301) can be chosen to maximize contrast relative to other original colors of the first image. For example, if the first image is associated with a surgical wound bed or a surgical tissue, then a green color or blue color can be chosen as the false color. In this case, the green or blue false color provides relatively better contrast with the red color tones typically present in images of this subject type.

Without being bound to any particular theory, the benefits of contrast-enhanced visual perception are likely to rely at least in part on the fundamental biophysics of photoreceptors in human visual system. In forming photo and color responses, photoreceptor cells are key parts of the visual phototransduction process. This process is used by the visual system to convert visible light to electrical signals that are transmitted to the visual cortex for processing into a visual image. The two classic photoreceptor cells are rod and cone cells, each using light-sensitive photoreceptor opsin proteins. The rods are sensitive to low light due to rhodopsin, one type of opsins, and particularly contribute to visual formation at low light levels. The cone cells are of three types, each with different photopsins. These react mostly to three different ranges of light bands having short, medium, and long frequencies. The three types of cones are thus sensitive to red, green, and blue bands with peaks at about 564-580 nm, 534-545 nm, and 420-440 nm, respectively. The cone cells are integral to color visual perception as well as motion information processed at the visual cortex. When expose to visible light, these photoreceptor cells are subject to overstimulation and can lose sensitivity in very short period of time due to tapering of the signal transduction in the photoreceptors even before fatigue occurs (such as afterimage). The use of complementary colors can work to alleviate this overstimulation and loss of sensitivity, and to enhance the perception of contrast.

The false color of the third image (203, 303) used to replace the selected original color of the first image (201, 301) can be chosen to have a selected hue, saturation, or value. The properties of colors can be described using several different parameters, including hue, chroma, purity, saturation, intensity, vividness, value, transparency, lightness, brightness, and darkness. One technique for describing colors is through the use of the three dimensions of hue, saturation, and value. These three dimensions can be visualized in cylindrical or conical models.

Figure 4:
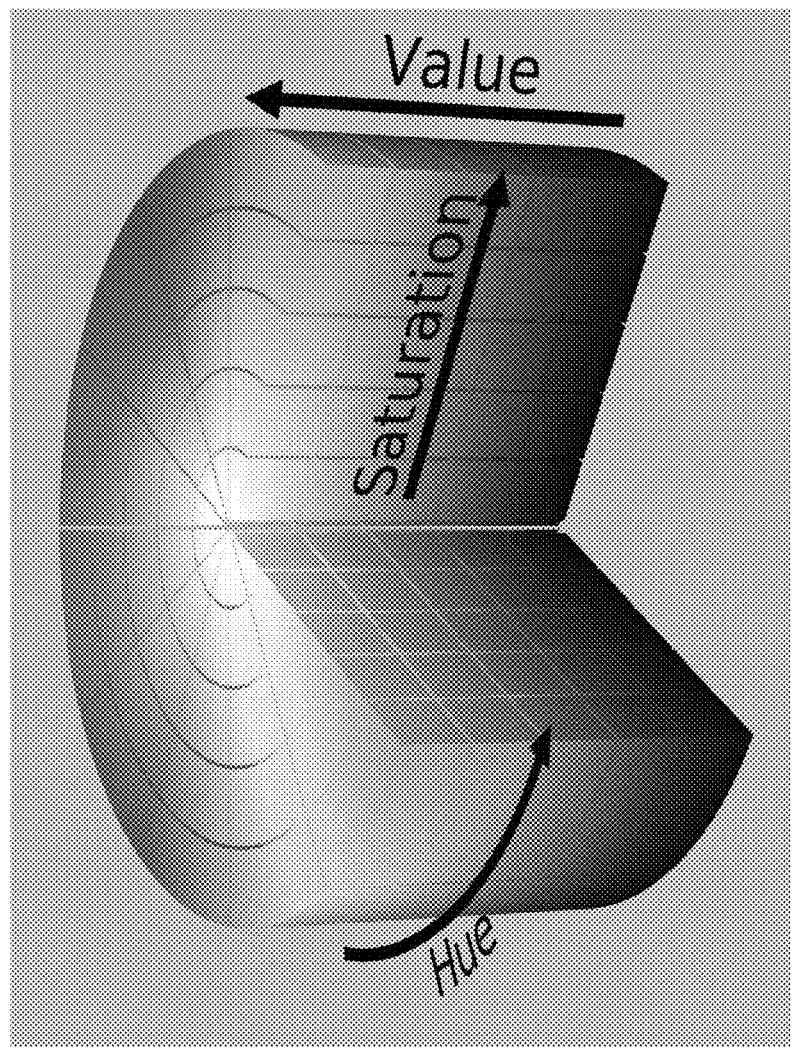
FIG. 4 illustrates a hue/saturation/value (HSV) cylindrical color space.

FIG. 4 illustrates a hue/saturation/value (HSV) cylindrical model color space. In this representation, different angular positions represent different color hues. Hue is the color property defined as degree to which a color is similar to a defined element of a color spectrum. These defined elements are typically referred to as pure hues of red, orange, yellow, green, blue, and purple or violet. Different radial distances within the model represent different color saturations. Color saturation, or color chroma, is the color property defined as the purity of a hue related to its dilution by white, gray, or black. Different height positions within the cylindrical space represent different color values. Color value is the color property defined as indicating the lightness or darkness of a color.

Other color spaces that can be used to define and select colors for use with the disclosed methods include International Commission on Illumination (CIE) models (such as CIE 1931 XYZ, CIELUV, CIELAB, and CIEUVW), red/green/blue (RGB) models (such as RGB, sRGB, Adobe RGB, and Adobe Wide Gamut RGB), luma plus chroma models (such as YIQ, YUV, YDbDr, YPbPr, YVbCr, and xvYCC), hue/saturation/lightness (HSL) models, and cyan/magenta/yellow/key (CMYK) models. Additive or subtractive color models can be used.

In some embodiments, the false color of the third image (203, 303) is chosen to have a color hue complementary to that of the selected original color of the first image (201, 301). Colors with complementary hues are those that are on opposite sides of the HSV color space as in the radial direction of the color model of FIG. 4. In some embodiments, the false color of the third image is chosen to have a color saturation different from that of the selected original color of the first image. In some embodiments, the false color of the third image is chosen to have a color value different from that of the selected original color of the first image. In some embodiments, the false color of the third image is chosen to have a color value that is within the range between the maximum and minimum color values of all original colors of the first image. In some embodiments, the false color of the third image is chosen to have a transparency such that it does not block relevant information of the second image (202, 302) upon rendering of the composite fifth image (205, 305).

The production of the fourth image (204, 304) can comprise the use of a computer system and a computation algorithm to replace the one or more selected original colors from the first image (201, 301). In some embodiments, the fourth image is stored subsequent to its generation and prior to its use in rendering the sixth image (206, 306). In some embodiments, the fourth image is used to render the sixth image directly after the generation of the fourth image.

The false color used to replace the selected original color of the first image (201, 301) can be chosen to maximize contrast relative to the false color of the third image (203, 303). For example, in FIG. 3, the false color of the third image 303 has a red hue and the false color of the fourth image 304 has the complementary green hue. As another example, if the false color of the third image has a blue hue, then the false color of the fourth image can be selected to have a yellow hue. If the false color of the third image has a green hue, then the false color of the fourth image can be selected to have a red hue. If the false color of the third image has a yellow hue, then the false color of the fourth image can be selected to have a blue hue. If the false color of the third image is white, then the false color of the fourth image can be selected to be black. If the false color of the third image is black, then the false color of the fourth image can be selected to be white.

In some embodiments, the false color of the fourth image (204, 304) is chosen to have a color hue complementary to that of the false color of the third image (203, 303). In some embodiments, the false color of the fourth image is chosen to have a color saturation different from that of the false color of the third image. In some embodiments, the false color of the fourth image is chosen to have a color value different from that of the false color of the third image. In some embodiments, the false color of the fourth image is chosen to have a color value that is within the range between the maximum and minimum color values of all original colors of the first image (201, 301). In some embodiments, the false color of the fourth image is chosen to have a transparency such that it does not block relevant information of the second image (202, 302) upon rendering of the composite sixth image (206, 306). In some embodiments, the transparency of the false colors of the third and fourth images are similar or identical.

In some embodiments, green and red hues are selected for the false colors of the third (203, 303) and fourth images (204, 304). In some embodiments, the red hue of one of the false colors is very close to the predominant hue of the underlying tissue that is the subject of the images. However, even in these embodiments the complementary color combination refreshes the visual photoreceptors and the dynamic flashing motion enhances the recognition sensitivity of the visual system.

The rendering of the fifth image (205, 305) is accomplished by overlaying the second image (202, 302) and the third image (203, 303). In some embodiments, the fifth image is a composite image that is stored subsequent to its rendering and prior to its displaying. In some embodiments, the fifth image is rendered with the use of a computer system and computational algorithm to digitally combine the second image and the third image in creating a fifth image. In some embodiments, the fifth image is rendered by simultaneously displaying the second image and the third image to create a superimposed fifth image.

The constructing of the sixth image (206, 306) is accomplished by overlaying the second image (202, 302) and the fourth image (204, 304). In some embodiments, the sixth image is a composite image that is stored subsequent to its rendering and prior to its displaying. In some embodiments, the sixth image is constructed with the use of a computer system and computational algorithm to digitally combine the second image and the fourth image in creating a sixth image. In some embodiments, the sixth image is constructed by simultaneously displaying the second image and the fourth image to create a superimposed sixth image.

The fifth (205, 305) and sixth (206, 306) images are alternately presented on a display for viewing by the operator. The display can be a monitor, a screen, a detector, an eyepiece, or any other visual interface. The alternating display can dynamically enhance perceived contrast to help the human visual system better detect the signal and location of the flashing or flicking region of alternating color. This can be particularly important for cases in which a low signal level would result in a contrast within a static image that would be challenging for a user to ascertain with a required degree of certainty. In these cases, the flashing of complementary colors works to alleviate visual overstimulation and loss of sensitivity, and to enhance perceived contrast.

Figure 5:
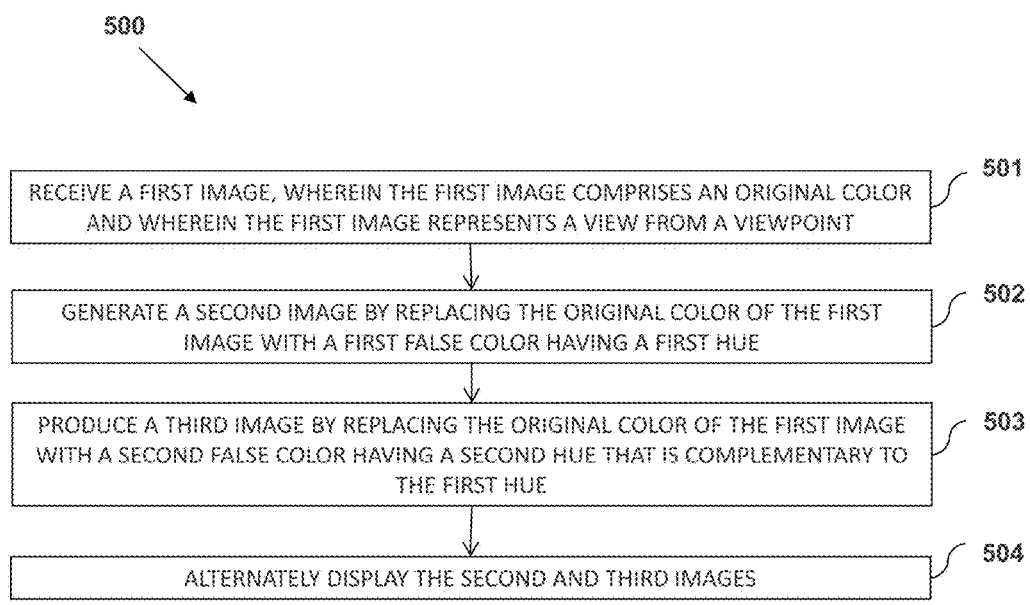
FIG. 5 is a flowchart of a process for alternately displaying two false color images derived from an imaging channel

FIG. 5 presents a flowchart of a process 500 for alternately displaying two false color images derived from an imaging channel. In operation 501, a first image is received, wherein the first image comprises an original color and wherein the first image represents a view from a viewpoint. In operation 502, a second image is generated by replacing the original color of the first image with a first false color having a first hue. In operation 503, a third image is produced by replacing the original color of the first image with a second false color having a second hue that is complementary to the first hue. In operation 504, the second and third images are alternately displayed.

Figure 6:
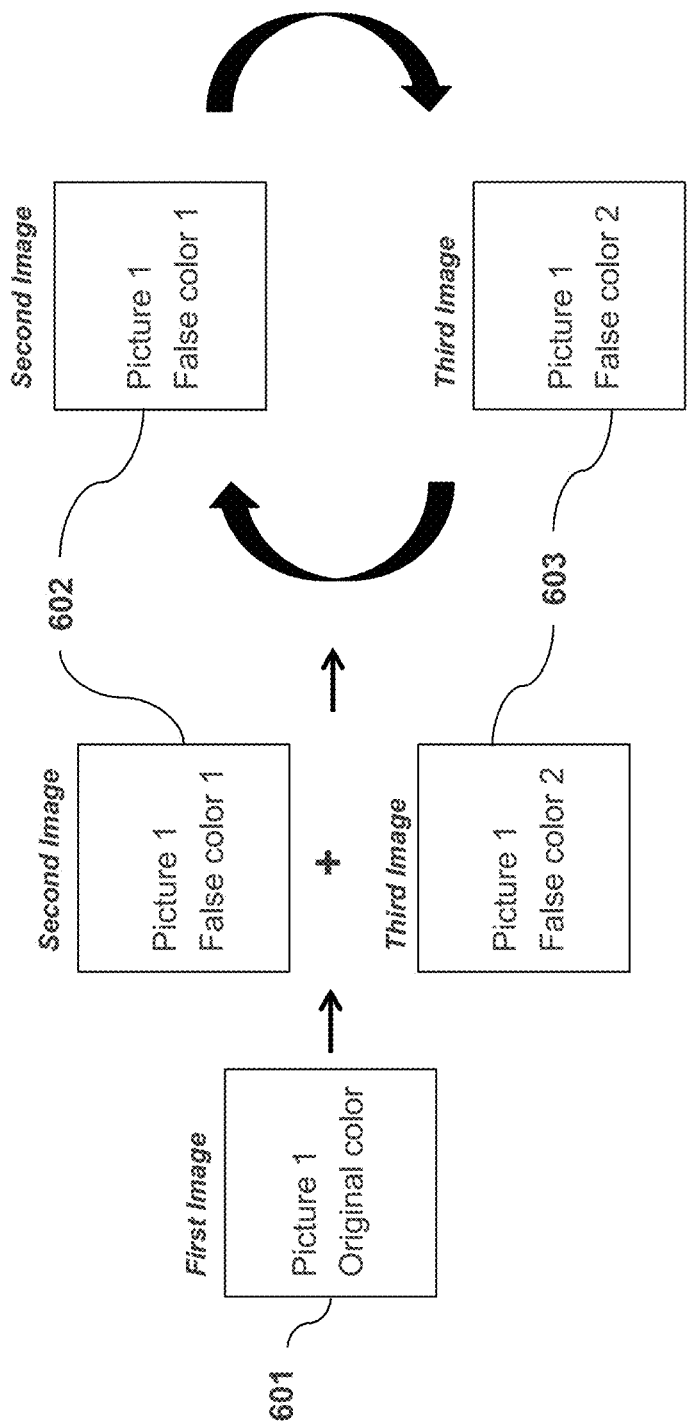
FIG. 6 is a schematic overview of an embodiment in accordance with the process of FIG. 5.

FIG. 6 provides a schematic overview of one embodiment in accordance with the process of FIG. 5. Shown is a first image 601. A second image 602 and a third image 603 are each generated or produced from the first image 601 by replacing an original color of the first image with a false color. The false color of the second image 602 has a first hue, and the false color of the third image 603 has a second hue. The second image 602 and the third image 603 are then alternately displayed.

Figure 7:
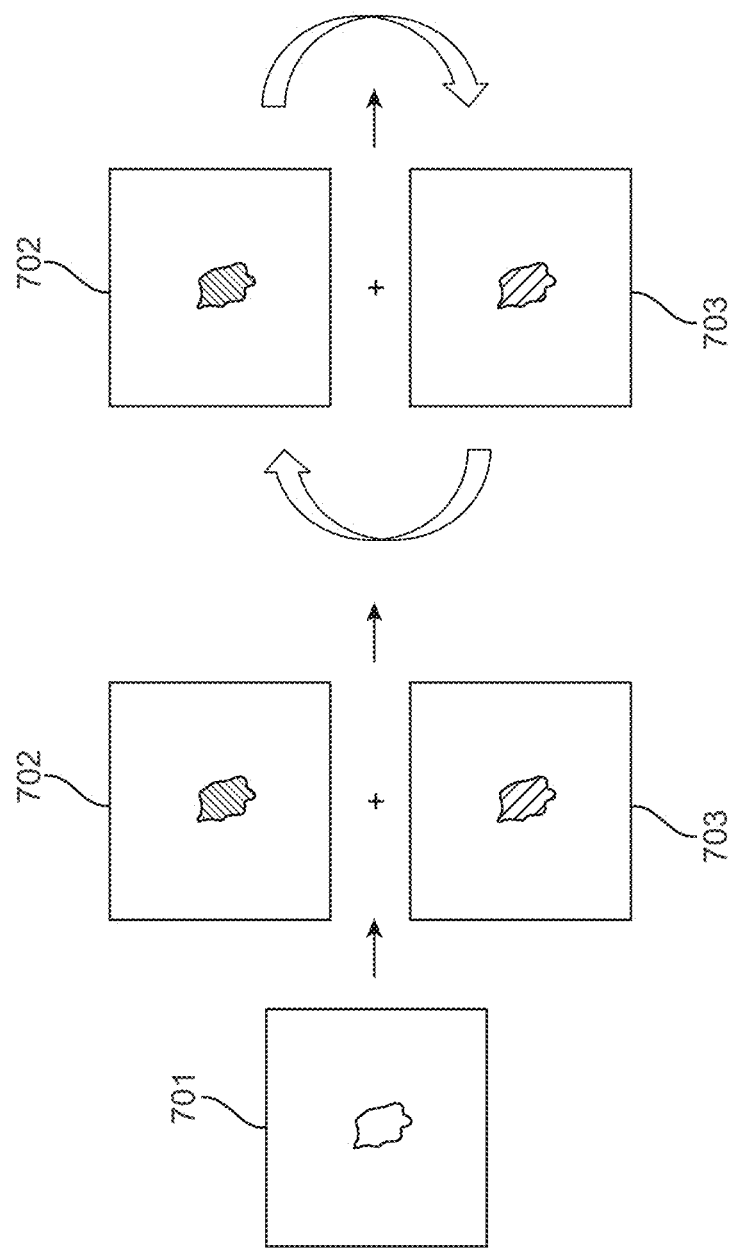
FIG. 7 is an illustration of an embodiment in accordance with the process of FIG. 5 and the schematic overview of FIG. 6.

FIG. 7 illustrates one embodiment in accordance with the process of FIG. 5 and the schematic overview of FIG. 6 as an example. Shown is a first image 701, which is a fluorescence image representing a biological sample as recorded using a fluorescence imaging channel or modality from a viewpoint. The original white color of the first image 701 is replaced by a false red color to generate a second image 702. The original white color of the first image 701 is replaced by a false green color to produce a third image 703. The second image 702 and the third image 703 are then alternately displayed. The complementarity of the red and green hues of the second 702 and third 703 images, as well as the dynamic presentation of the second and third images, allow a user to better discern the features of the original fluorescence image 701.

The first image (601, 701) can be any visual representation having a feature of interest. In some embodiments, as in FIG. 7, the first image 701 is a fluorescence image of a biological sample. The first image can be a composite image of two or more imaging modalities, of two or more subjects and/or of two or more viewpoints. The first image can comprise information recorded of a physical object or scene. For example, the first image can be a photographic or tomographic image recorded using one or more imaging modalities. The first image can be a representation of a physical or abstract object or scene. For example, the first image can be of an illustration, a sketch, a computer-generated model, or a painting. The first image can be a static image or can be a frame of a video.

The first image (601, 701) can comprise any imaging modalities. In some embodiments, as in FIG. 7, the first image 701 comprises a fluorescence imaging modality. The first image can comprise an imaging modality of reflected light, X-ray, CT, MRI, PET, SPECT, or ultrasound. In some embodiments, the first image comprises a single imaging modality. In some embodiments, the first image comprises two or more imaging modalities.

The first image (601, 701) can be received from any source. In some embodiments, the first image is retrieved from a computer memory system. In some embodiments, the first image is transmitted from a source that can be local or remote relative to the location of the image processing of the disclosed methods. In some embodiments, the first image is input, entered, or submitted by an operator. In some embodiments, the first image is recorded using a camera or imager for use with one of the disclosed method. In some embodiments, the first image is recorded using a camera or imager and is stored using a computer memory system prior to its being retrieved or transmitted for use with one of the disclosed methods.

One or more cameras or imagers can be used to record the first image (601, 701). The camera or imager can be configured to capture still images or video or movie images. The camera or imager can be configured to have any functional lens assembly, focal length, and exposure control sufficient to record the first image. The camera or imager can record the first image using a plate or film. The camera or imager can record the first image using an electronic image sensor. The camera or imager can comprise a charged coupled device (CCD) and/or a complementary metal-oxide-semiconductor (CMOS) sensor.

The first image (601, 701) comprises one or more original colors. In some embodiments, as in FIG. 7, the first image is a monochromatic image. In some embodiments, the first image comprises two or more colors. The reference to the one or more colors as being original colors is merely to specify that the colors are original to the first image, and not necessarily original to the subject of the first image. For example, electromagnetic radiation emitted or reflected by a subject at wavelengths outside of the spectrum visible to human perception can be represented by alternative visible wavelengths in a first image. In this example, the alternative wavelengths, while not original to the subject, are original to the first image representation of the subject, and are referred to herein as original colors.

As another example, a first image (601, 701) may represent data or information not associated with a color of a physical subject. This can be the case in representing, for example, data related to values for temperatures, pressures, concentrations, or any other non-visual parameter. In these cases, a first image can use a color scheme in which one or more colors are used to represent one or more different values or ranges of values for the non-visual parameters. In these examples, the representative colors are not original to a physical subject, but are original to the first image, and are referred to herein as original colors.

As a third example, a subject can emit or reflect electromagnetic radiation at visible wavelengths while a first image (601, 701) of the subject represents these visible colors with alternate colors. This can be the case, for example, when small differences between one or more colors emitted or reflected by the subject are exaggerated through the selection of an alternate color scheme. This can also be the case when the true colors reflected or emitted by a subject are difficult for at least some users to perceive. This can be the case, for example, with a population of users having one or more types of color blindness. In these examples, the alternative colors, while not original to the subject, are original to the first image representation of the subject, and are referred to herein as original colors.

The first image (601, 701) can be a view of a subject representative from a particular viewpoint. The view can be from any distance or angle relative to the subject. In some embodiments, the viewpoint is as least partially determined by the position of a camera or imager used to capture, record, store, or transmit the first image. In some embodiments, image manipulation is used such that the view is from a viewpoint other than the actual position of a camera or imager. Zooming, panning, or rotating functionalities can be used to alter the first image so that it represents a view from a different viewpoint in space. This different view can be the result of repositioning the camera or imager. The different view can be the result of selecting a different set of information that has been previously captured, recorded, stored, or transmitted while the camera or imager was in a different position. The different view can be the result of computer processing, such as with interpolation or extrapolation algorithms, to simulate a different position of the camera or imager.

The second image (602, 702) is generated from the first image (601, 701) by replacing one or more selected original colors from the first image with one or more false colors. In some embodiments, one original color from the first image is replaced with one false color in generating the second image. In some embodiments, two or more original colors from the first image are each replaced with one false color in generating the second image. The generation of the second image can comprise the use of a computer system and a computation algorithm to replace the one or more selected original colors from the first image.

The false color used to replace the selected original color of the first image (601, 701) can be chosen to maximize contrast relative to other original colors of the first image. For example, if the first image is associated with a surgical wound bed or a surgical tissue, then a green color or blue color can be chosen as the false color. In this case, the green or blue false color provides relatively better contrast with the red color tones typically present in images of this subject type.

The false color of the second image (602, 702) used to replace the selected original color of the first image (601, 701) can be chosen to have a selected hue, saturation, or value. In some embodiments, the false color of the second image is chosen to have a color hue complementary to that of the selected original color of the first image. In some embodiments, the false color of the second image is chosen to have a color saturation different from that of the selected original color of the first image. In some embodiments, the false color of the second image is chosen to have a color value different from that of the selected original color of the first image. In some embodiments, the false color of the second image is chosen to have a color value that is within the range between the maximum and minimum color values of all original colors of the first image.

The production of the third image (603, 703) can comprise the use of a computer system and a computation algorithm to replace the one or more selected original colors from the first image (601, 701). The false color used to replace the selected original color of the first image can be chosen to maximize contrast relative to the false color of the second image (602, 702). For example, in FIG. 7, the false color of the second image 702 has a red hue and the false color of the third image 703 has the complementary green hue. As another example, if the false color of the second image has a blue hue, then the false color of the third image can be selected to have a yellow hue. If the false color of the second image has a green hue, then the false color of the third image can be selected to have a red hue. If the false color of the second image has a yellow hue, then the false color of the third image can be selected to have a blue hue. If the false color of the second image is white, then the false color of the third image can be selected to be black. If the false color of the second image is black, then the false color of the third image can be selected to be white.

In some embodiments, the false color of the third image (603, 703) is chosen to have a color hue complementary to that of the false color of the second image (602, 702). In some embodiments, the false color of the third image is chosen to have a color saturation different from that of the false color of the second image. In some embodiments, the false color of the third image is chosen to have a color value different from that of the false color of the second image. In some embodiments, the false color of the third image is chosen to have a color value that is within the range between the maximum and minimum color values of all original colors of the first image (601, 701).

The second (602, 702) and third (603, 703) images are alternately presented on a display for viewing by the operator. The display can be a monitor, a screen, a detector, an eyepiece, or any other visual interface. The alternating display can dynamically enhance perceived contrast to help the human visual system better detect the signal and location of the flashing or flicking region of alternating color. This can be particularly important for cases in which a low signal level would result in a contrast within a static image that would be challenging for a user to ascertain with a required degree of certainty. In these cases, the flashing of complementary colors works to alleviate visual overstimulation and loss of sensitivity, and to enhance perceived contrast.

Figure 8:
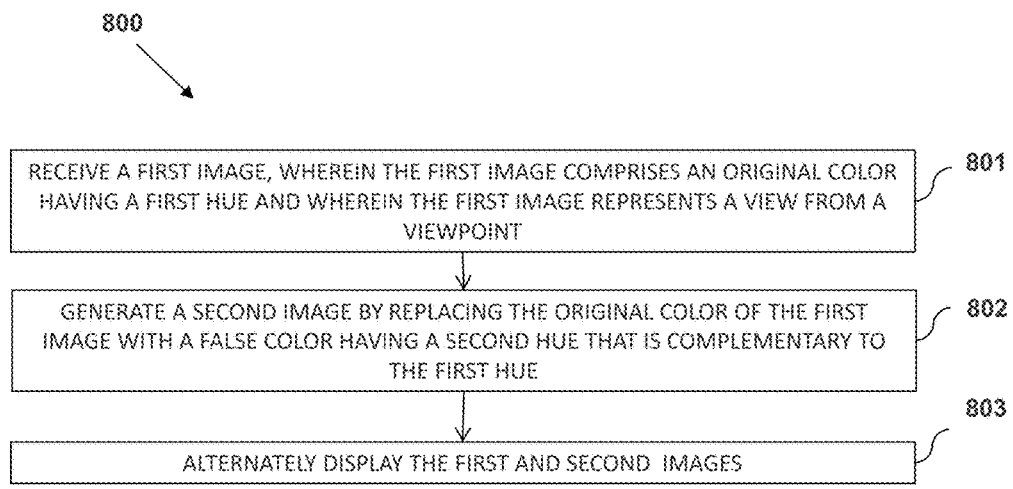
FIG. 8 is a flowchart of a process for alternately displaying a false color images derived from an imaging channel and an original color image from the imaging channel.

FIG. 8 presents a flowchart of a process 800 for alternately displaying a false color image derived from an imaging channel and an original color image from the imaging channel. In operation 801, a first image is received, wherein the first image comprises an original color having a first hue and wherein the first image represents a view from a viewpoint. In operation 802, a second image is generated by replacing the original color of the first image with a false color having a second hue that is complementary to the first hue. In operation 803, the first and second images are alternately displayed.

Figure 9:
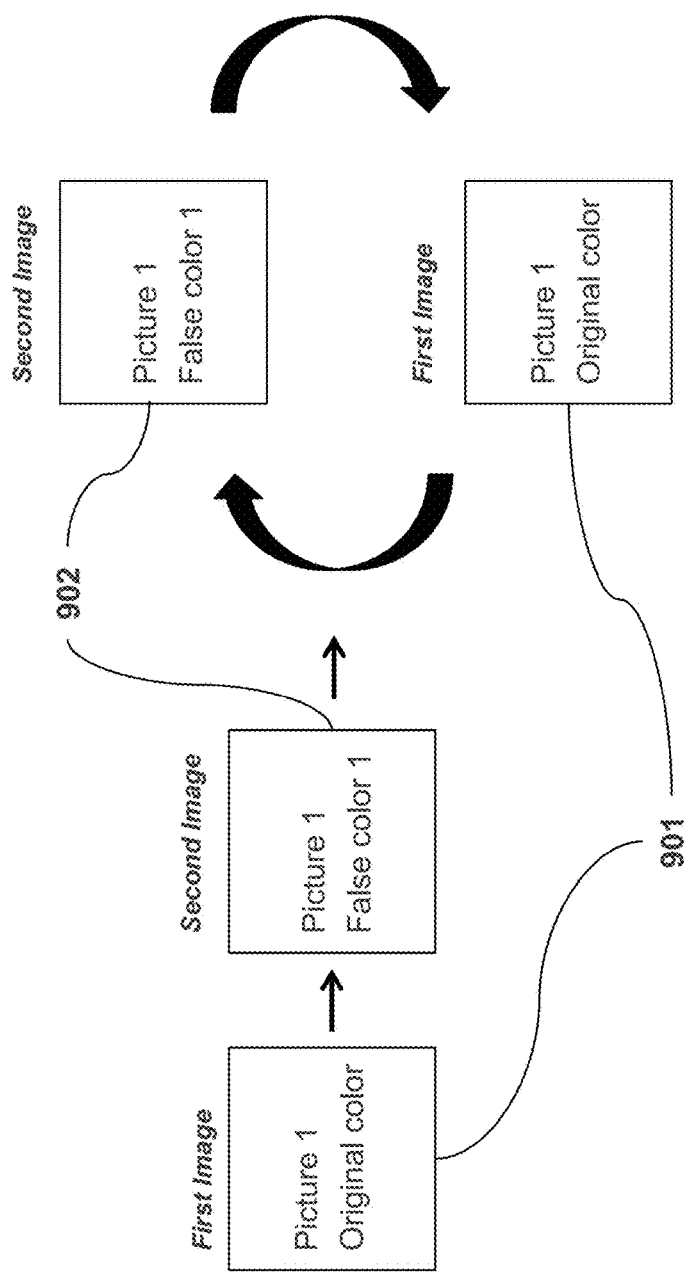
FIG. 9 is a schematic overview of an embodiment in accordance with the process of FIG. 8.

FIG. 9 provides a schematic overview of one embodiment in accordance with the process of FIG. 8. Shown is a first image 901 having an original color having a first hue. A second image 902 is generated or produced from the first image 901 by replacing the original color of the first image with a false color having a second hue. The first image 901 and the second image 902 are then alternately displayed.

Figure 10:
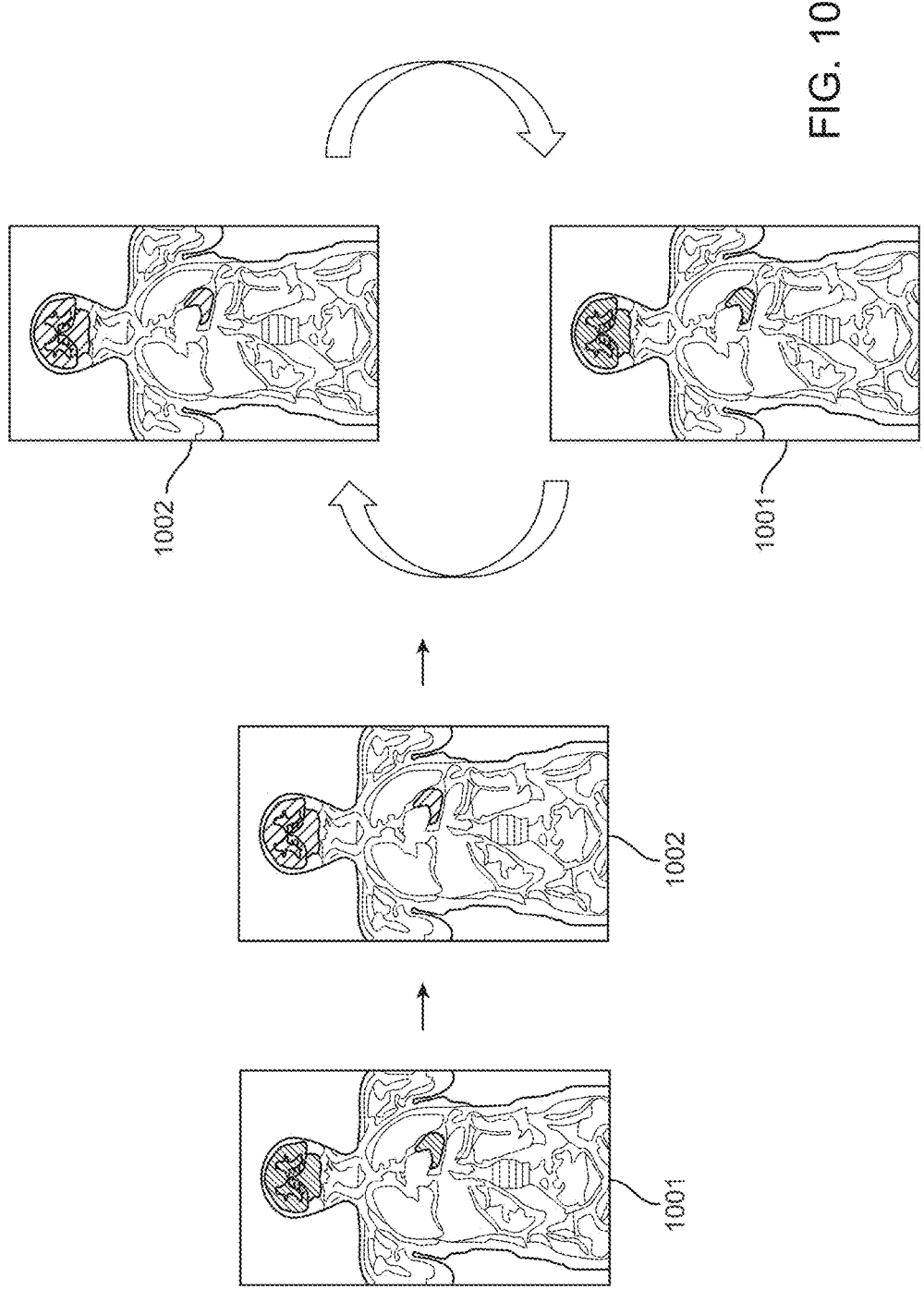
FIG. 10 is an illustration of an embodiment in accordance with the process of FIG. 8 and the schematic overview of FIG. 9.

FIG. 10 illustrates one embodiment in accordance with the process of FIG. 8 and the schematic overview of FIG. 9 as an example. Shown is a first image 1001, which is a PET-MM fusion image representing a biological sample as recorded using both a PET imaging channel or modality and an MRI imaging channel or modality, each from the same viewpoint. The original red color of the first image 1001 is replaced by a false green color to generate a second image 1002. The first image 1001 and the second image 1002 are then alternately displayed. The complementarity of the red and green hues of the first 1001 and second 1002 images, as well as the dynamic presentation of the first and second images, allow a user to better discern the features of the original PET-MRI image 1001.

The first image (901, 1001) can be any visual representation having a feature of interest. In some embodiments, as in FIG. 10, the first image 1001 is a PET-MRI fusion image of a biological sample. The first image can be a composite image of two or more imaging modalities, of two or more subjects and/or of two or more viewpoints. The first image can comprise information recorded of a physical object or scene. For example, the first image can be a photographic or tomographic image recorded using one or more imaging modalities. The first image can be a representation of a physical or abstract object or scene. For example, the first image can be of an illustration, a sketch, a computer-generated model, or a painting. The first image can be a static image or can be a frame of a video.

The first image (901, 1001) can comprise any imaging modalities. In some embodiments, as in FIG. 10, the first image 1001 comprises both a PET imaging modality and an MRI imaging modality. The first image can comprise an imaging modality of reflected light, X-ray, computerized tomography (CT), fluorescence, SPECT, or ultrasound. In some embodiments, the first image comprises a single imaging modality. In some embodiments, the first image comprises two or more imaging modalities.

The first image (901, 1001) can be received from any source. In some embodiments, the first image is retrieved from a computer memory system. In some embodiments, the first image is transmitted from a source that can be local or remote relative to the location of the image processing of the disclosed methods. In some embodiments, the first image is input, entered, or submitted by an operator. In some embodiments, the first image is recorded using a camera or imager for use with one of the disclosed method. In some embodiments, the first image is recorded using a camera or imager and is stored using a computer memory system prior to its being retrieved or transmitted for use with one of the disclosed methods.

One or more cameras or imagers can be used to record the first image (901, 1001). The camera or imager can be configured to capture still images or video or movie images. The camera or imager can be configured to have any functional lens assembly, focal length, and exposure control sufficient to record the first image. The camera or imager can record the first image using a plate or film. The camera or imager can record the first image using an electronic image sensor. The camera or imager can comprise a charged coupled device (CCD) and/or a complementary metal-oxide-semiconductor (CMOS) sensor.

The first image (901, 1001) comprises one or more original colors. In some embodiments, the first image is a monochromatic image. In some embodiments, as in FIG. 10, the first image comprises two or more colors. The reference to the one or more colors as being original colors is merely to specify that the colors are original to the first image, and not necessarily original to the subject of the first image. For example, electromagnetic radiation emitted or reflected by a subject at wavelengths outside of the spectrum visible to human perception can be represented by alternative visible wavelengths in a first image. In this example, the alternative wavelengths, while not original to the subject, are original to the first image representation of the subject, and are referred to herein as original colors.

As another example, a first image (901, 1001) may represent data or information not associated with a color of a physical subject. This can be the case in representing, for example, data related to values for temperatures, pressures, concentrations, or any other non-visual parameter. In these cases, a first image can use a color scheme in which one or more colors are used to represent one or more different values or ranges of values for the non-visual parameters. In these examples, the representative colors are not original to a physical subject, but are original to the first image, and are referred to herein as original colors.

As a third example, a subject can emit or reflect electromagnetic radiation at visible wavelengths while a first image (901, 1001) of the subject represents these visible colors with alternate colors. This can be the case, for example, when small differences between one or more colors emitted or reflected by the subject are exaggerated through the selection of an alternate color scheme. This can also be the case when the true colors reflected or emitted by a subject are difficult for at least some users to perceive. This can be the case, for example, with a population of users having one or more types of color blindness. In these examples, the alternative colors, while not original to the subject, are original to the first image representation of the subject, and are referred to herein as original colors.

The first image (901, 1001) can be a view of a subject representative from a particular viewpoint. The view can be from any distance or angle relative to the subject. In some embodiments, the viewpoint is as least partially determined by the position of a camera or imager used to capture, record, store, or transmit the first image. In some embodiments, image manipulation is used such that the view is from a viewpoint other than the actual position of a camera or imager. Zooming, panning, or rotating functionalities can be used to alter the first image so that it represents a view from a different viewpoint in space. This different view can be the result of repositioning the camera or imager. The different view can be the result of selecting a different set of information that has been previously captured, recorded, stored, or transmitted while the camera or imager was in a different position. The different view can be the result of computer processing, such as with interpolation or extrapolation algorithms, to simulate a different position of the camera or imager.

The second image (902, 1002) is generated from the first image (901, 1001) by replacing one or more selected original colors from the first image with one or more false colors. In some embodiments, one original color from the first image is replaced with one false color in generating the second image. In some embodiments, two or more original colors from the first image are each replaced with one false color in generating the second image. The generation of the second image can comprise the use of a computer system and a computation algorithm to replace the one or more selected original colors from the first image.

The false color used to replace the selected original color of the first image (901, 1001) can be chosen to maximize contrast relative to other original colors of the first image. For example, if the first image is associated with a surgical wound bed or a surgical tissue, then a green color or blue color can be chosen as the false color. In this case, the green or blue false color provides relatively better contrast with the red color tones typically present in images of this subject type.

The false color of the second image (902, 1002) used to replace the selected original color of the first image (901, 1001) can be chosen to have a selected hue, saturation, or value. In some embodiments, the false color of the second image is chosen to have a color hue complementary to that of the selected original color of the first image. In some embodiments, the false color of the second image is chosen to have a color saturation different from that of the selected original color of the first image. In some embodiments, the false color of the second image is chosen to have a color value different from that of the selected original color of the first image. In some embodiments, the false color of the second image is chosen to have a color value that is within the range between the maximum and minimum color values of all original colors of the first image.

The first (901, 1001) and second (902, 1002) images are alternately presented on a display for viewing by the operator. The display can be a monitor, a screen, a detector, an eyepiece, or any other visual interface. The alternating display can dynamically enhance perceived contrast to help the human visual system better detect the signal and location of the flashing or flicking region of alternating color. This can be particularly important for cases in which a low signal level would result in a contrast within a static image that would be challenging for a user to ascertain with a required degree of certainty. In these cases, the flashing of complementary colors works to alleviate visual overstimulation and loss of sensitivity, and to enhance perceived contrast.

Figure 11:
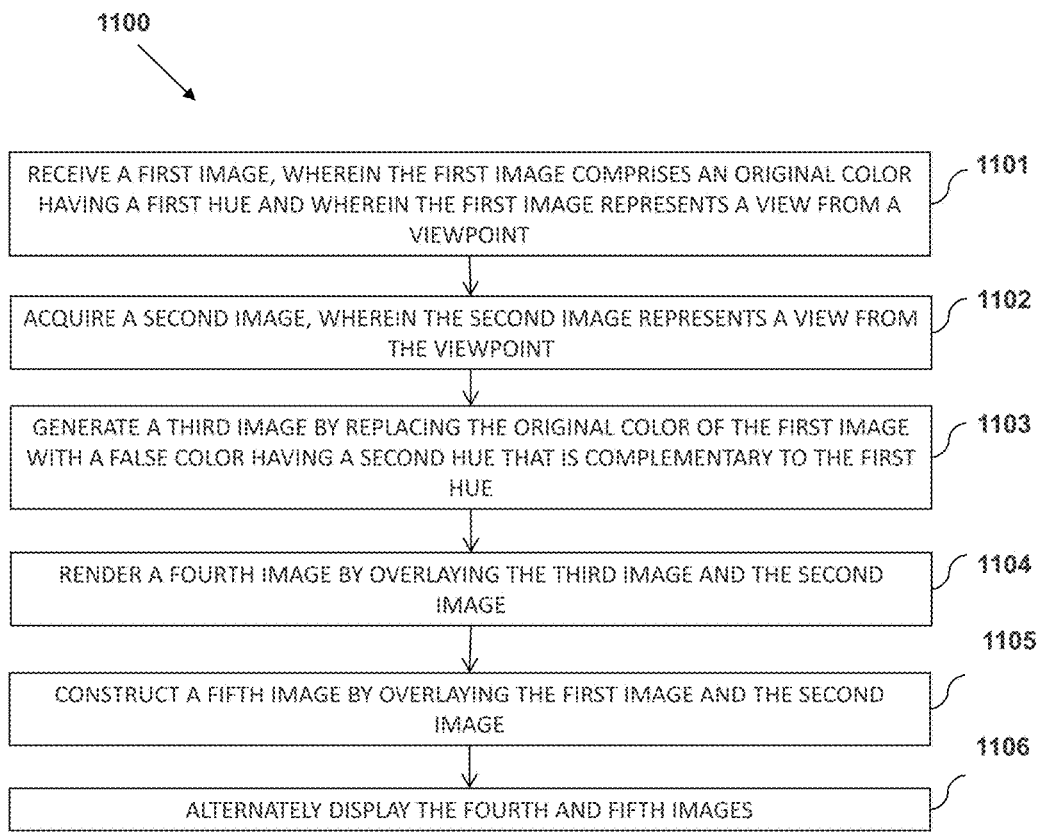
FIG. 11 is a flowchart of a process for alternately displaying a false color images derived from an imaging channel and an original color image from the imaging channel, each of the images overlaid on an image from a second imaging channel.

FIG. 11 presents a flowchart of a process 1100 for alternately displaying a false color image derived from a first imaging channel and an original color image derived from the imaging channel, each of the images overlaid on an image from a second imaging channel. In operation 1101, a first image is received, wherein the first image comprises an original color having a first hue and wherein the first image represents a view from a viewpoint. In operation 1102, a second image is acquired, wherein the second image represents a view from the viewpoint. In operation 1103, a third image is generated by replacing the original color of the first image with a false color having a second hue that is complementary to the first hue. In operation 1104, a fourth image is rendered by overlaying the third image and the second image. In operation 1105, a fifth image is constructed by overlaying the first image and the second image. In operation 1106, the fourth and fifth images are alternately displayed.

Figure 12:
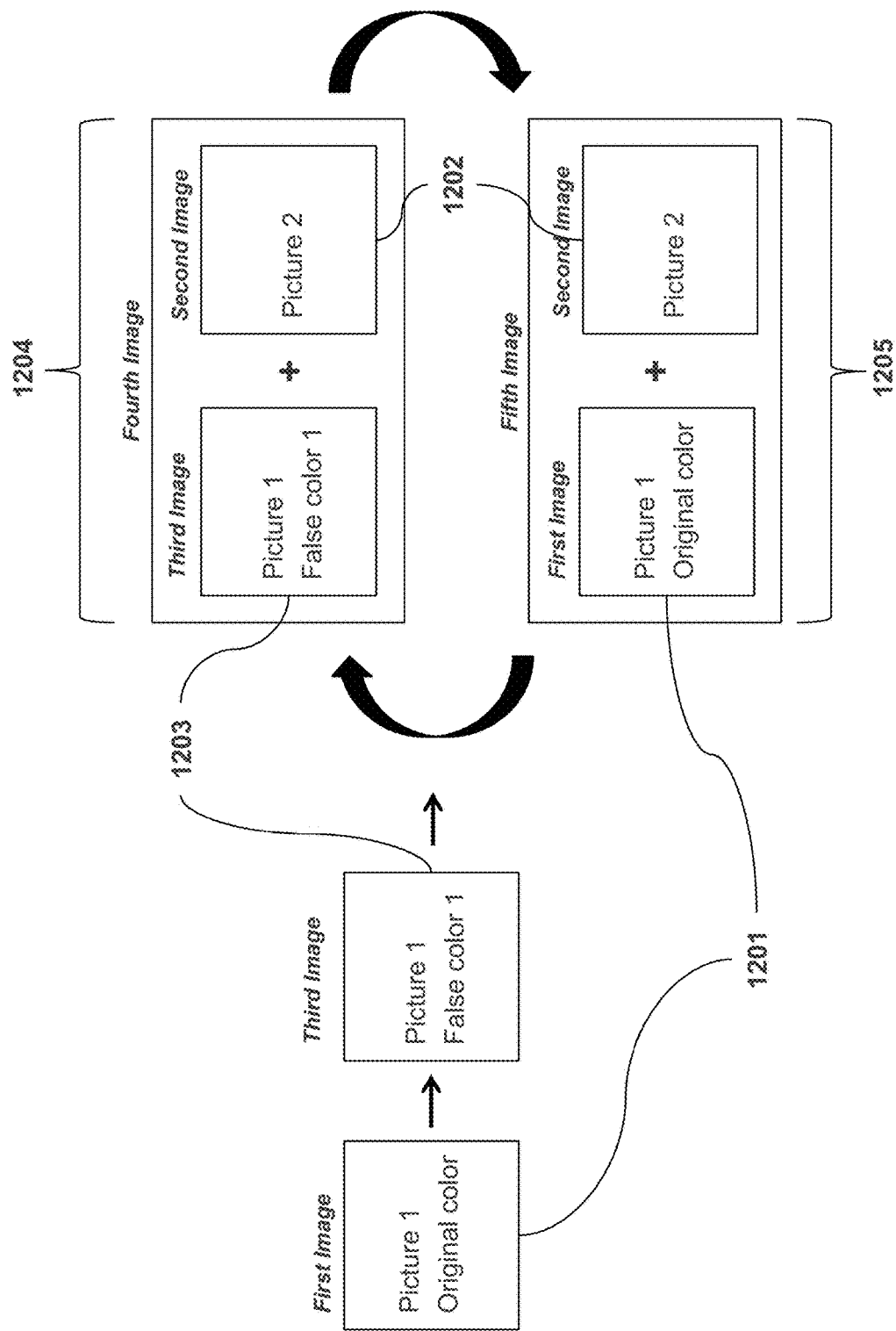
FIG. 12 is a schematic overview of an embodiment in accordance with the process of FIG. 11.

FIG. 12 provides a schematic overview of one embodiment in accordance with the process of FIG. 1. Shown are a first image 1201 and a second image 1202. A third image 1203 is generated from the first image 1201 by replacing an original color of the first image with a false color. The original color of the first image 1201 has a first hue, and the false color of the third image 1203 has a second hue. The second hue is complementary to the first hue. A fourth image 1204 is rendered by overlaying the third image 1203 and the second image 1202. A fifth image 1205 is constructed by overlaying the first image 1201 and the second image 1202. The fourth image 1204 and the fifth image 1205 are then alternately displayed.

The first image 1201 can be any visual representation having a feature of interest. The first image can be a composite image of two or more imaging modalities, of two or more subjects and/or of two or more viewpoints. The first image can comprise information recorded of a physical object or scene. For example, the first image can be a photographic or tomographic image recorded using one or more imaging modalities. The first image can be a representation of a physical or abstract object or scene. For example, the first image can be of an illustration, a sketch, a computer-generated model, or a painting. The first image can be a static image or can be a frame of a video.

The first image 1201 can comprise any imaging modalities. The first image can comprise an imaging modality of reflected light, X-ray, CT, fluorescence, MRI, PET, SPECT, or ultrasound. In some embodiments, the first image comprises a single imaging modality. In some embodiments, the first image comprises two or more imaging modalities.

The first image 1201 can be received from any source. In some embodiments, the first image is retrieved from a computer memory system. In some embodiments, the first image is transmitted from a source that can be local or remote relative to the location of the image processing of the disclosed methods. In some embodiments, the first image is input, entered, or submitted by an operator. In some embodiments, the first image is recorded using a camera or imager for use with one of the disclosed method. In some embodiments, the first image is recorded using a camera or imager and is stored using a computer memory system prior to its being retrieved or transmitted for use with one of the disclosed methods.

One or more cameras or imagers can be used to record the first image 1201. The camera or imager can be configured to capture still images or video or movie images. The camera or imager can be configured to have any functional lens assembly, focal length, and exposure control sufficient to record the first image. The camera or imager can record the first image using a plate or film. The camera or imager can record the first image using an electronic image sensor. The camera or imager can comprise a charged coupled device (CCD) and/or a complementary metal-oxide-semiconductor (CMOS) sensor.

The first image 1201 comprises one or more original colors. In some embodiments, the first image is a monochromatic image. In some embodiments, the first image comprises two or more colors. The reference to the one or more colors as being original colors is merely to specify that the colors are original to the first image, and not necessarily original to the subject of the first image. For example, electromagnetic radiation emitted or reflected by a subject at wavelengths outside of the spectrum visible to human perception can be represented by alternative visible wavelengths in a first image. In this example, the alternative wavelengths, while not original to the subject, are original to the first image representation of the subject, and are referred to herein as original colors.

As another example, a first image 1201 may represent data or information not associated with a color of a physical subject. This can be the case in representing, for example, data related to values for temperatures, pressures, concentrations, or any other non-visual parameter. In these cases, a first image can use a color scheme in which one or more colors are used to represent one or more different values or ranges of values for the non-visual parameters. In these examples, the representative colors are not original to a physical subject, but are original to the first image, and are referred to herein as original colors.

As a third example, a subject can emit or reflect electromagnetic radiation at visible wavelengths while a first image 1201 of the subject represents these visible colors with alternate colors. This can be the case, for example, when small differences between one or more colors emitted or reflected by the subject are exaggerated through the selection of an alternate color scheme. This can also be the case when the true colors reflected or emitted by a subject are difficult for at least some users to perceive. This can be the case, for example, with a population of users having one or more types of color blindness. In these examples, the alternative colors, while not original to the subject, are original to the first image representation of the subject, and are referred to herein as original colors.

The first image 1201 can be a view of a subject representative from a particular viewpoint. The view can be from any distance or angle relative to the subject. In some embodiments, the viewpoint is as least partially determined by the position of a camera or imager used to capture, record, store, or transmit the first image. In some embodiments, image manipulation is used such that the view is from a viewpoint other than the actual position of a camera or imager. Zooming, panning, or rotating functionalities can be used to alter the first image so that it represents a view from a different viewpoint in space. This different view can be the result of repositioning the camera or imager. The different view can be the result of selecting a different set of information that has been previously captured, recorded, stored, or transmitted while the camera or imager was in a different position. The different view can be the result of computer processing, such as with interpolation or extrapolation algorithms, to simulate a different position of the camera or imager.

The second image 1202 can be any visual representation from the same one or more viewpoints as that of the first image. The second image can be a composite image of two or more imaging modalities, of two or more subjects and/or of two or more viewpoints. The second image can comprise information recorded of a physical object or scene. For example, the second image can be a photographic or tomographic image recorded using one or more imaging modalities. The second image can be a representation of a physical or abstract object or scene. For example, the second image can be of an illustration, a sketch, a computer-generated model, or a painting. The second image can be a static image or can be a frame of a video.

The second image 1202 can comprise any imaging modalities. The second image can comprise an imaging modality of reflected light, fluorescence, X-ray, CT, MRI, PET, SPECT, or ultrasound. In some embodiments, the second image comprises a single imaging modality. In some embodiments, the second image comprises two or more imaging modalities.

The second image 1202 can be received from any source. In some embodiments, the second image is retrieved from a computer memory system. In some embodiments, the second image is transmitted from a source that can be local or remote relative to the location of the image processing of the disclosed methods. In some embodiments, the second image is input, entered, or submitted by an operator. In some embodiments, the second image is recorded using a camera or imager for use with one of the disclosed method. In some embodiments, the second image is recorded using a camera or imager and is stored using a computer memory system prior to its being retrieved or transmitted for use with one of the disclosed methods.

One or more cameras or imagers can be used to record the second image 1202. The camera or imager can be configured to capture still images or video or movie images. The camera or imager can be configured to have any functional lens assembly, focal length, and exposure control sufficient to record the second image. The camera or imager can record the second image using a plate or film. The camera or imager can record the second image using an electronic image sensor. The camera or imager can comprise a charged coupled device (CCD) and/or a complementary metal-oxide-semiconductor (CMOS) sensor. In some embodiments, the same camera or imager is used to record or capture both the first 1201 and second image. In some embodiments, a first camera or imager is used to record or capture the first image, and a second camera or imager is used to record or capture the second image.

The third image 1203 is generated from the first image 1201 by replacing one or more selected original colors from the first image with one or more false colors. In some embodiments, one original color from the first image is replaced with one false color in generating the third image. In some embodiments, two or more original colors from the first image are each replaced with one false color in generating the third image.

The generation of the third image 1203 can comprise the use of a computer system and a computation algorithm to replace the one or more selected original colors from the first image 1201. In some embodiments, the third image is stored subsequent to its generation and prior to its use in rendering the fourth image 1204. In some embodiments, the third image is used to render the fourth image directly after the generation of the third image.

The false color used to replace the selected original color of the first image 1201 can be chosen to maximize contrast relative to other original colors of the first image. For example, if the first image is associated with a surgical wound bed or a surgical tissue, then a green color or blue color can be chosen as the false color. In this case, the green or blue false color provides relatively better contrast with the red color tones typically present in images of this subject type.

The false color of the third image 1203 used to replace the selected original color of the first image 1201 can be chosen to have a selected hue, saturation, or value. In some embodiments, the false color of the third image is chosen to have a color hue complementary to that of the selected original color of the first image. In some embodiments, the false color of the third image is chosen to have a color saturation different from that of the selected original color of the first image. In some embodiments, the false color of the third image is chosen to have a color value different from that of the selected original color of the first image. In some embodiments, the false color of the third image is chosen to have a color value that is within the range between the maximum and minimum color values of all original colors of the first image. In some embodiments, the false color of the third image is chosen to have a transparency such that it does not block relevant information of the second image 1202 upon rendering of the composite fourth image 1204.

The rendering of the fourth image 1204 is accomplished by overlaying the second image 1202 and the third image 1203. In some embodiments, the fourth image is a composite image that is stored subsequent to its rendering and prior to its displaying. In some embodiments, the fourth image is rendered with the use of a computer system and computational algorithm to digitally combine the second image and the third image in creating a fourth image. In some embodiments, the fourth image is rendered by simultaneously displaying the second image and the third image to create a superimposed fourth image.

The constructing of the fifth image 1205 is accomplished by overlaying the first image 1201 and the second image 1202. In some embodiments, the fifth image is a composite image that is stored subsequent to its rendering and prior to its displaying. In some embodiments, the fifth image is constructed with the use of a computer system and computational algorithm to digitally combine the first image and the second image in creating a fifth image. In some embodiments, the fifth image is constructed by simultaneously displaying the first image and the second image to create a superimposed sixth image.

The fourth 1204 and fifth 1205 images are alternately presented on a display for viewing by the operator. The display can be a monitor, a screen, a detector, an eyepiece, or any other visual interface. The alternating display can dynamically enhance perceived contrast to help the human visual system better detect the signal and location of the flashing or flicking region of alternating color. This can be particularly important for cases in which a low signal level would result in a contrast within a static image that would be challenging for a user to ascertain with a required degree of certainty. In these cases, the flashing of complementary colors works to alleviate visual overstimulation and loss of sensitivity, and to enhance perceived contrast.

The alternately displaying of any of the above methods can be performed at a selected frequency. The frequency can be chosen to correspond with ranges appropriate for improving human visual perception. The frequency can be further chosen to enhance visual sensitization. The frequency can be, for example, between 0.1 Hz and 60 Hz, between 0.1 Hz and 30 Hz, between 15 Hz and 45 Hz, between 30 Hz and 60 Hz, between 0.1 Hz and 20 Hz, between 10 Hz and 30 Hz, between 20 Hz and 40 Hz, between 30 Hz and 50 Hz, between 40 Hz and 60 Hz, between, 0.1 Hz and 10 Hz, between 5 Hz and 15 Hz, between 10 Hz and 20 Hz, or between 15 Hz and 25 Hz. In some embodiments, the frequency of the alternately displaying is between 0.1 Hz and 25 Hz.

The alternately displaying can be performed at a fixed selected frequency. The alternately displaying can be performed at a changing frequency. The frequency changes can be used to indicate additional information. The additional information can be related to, for example, the significance of information present in the alternately displayed images, a warning, an identification, or other.

Any of the above methods can further comprise accepting operator input selecting the frequency of the alternately displaying. Any of the above methods can further comprise accepting operator input selecting the viewpoint. Any of the above methods can further comprise accepting operator input selecting a region of an image. Operator input can be entered using any systems or methods effective for computer control. In some embodiments, operator input is entered using key or button presses. In some embodiments, operator input is entered using voice commands. In some embodiments, operator input is entered using accelerometers. In some embodiments, operator input is entered using gestures. In some embodiments, operator input is entered using manipulation of one or more control sticks. In some embodiments, operator input is entered using touch. The selection of a viewpoint using touch can comprise, for example, pinch commands to select viewpoints closer to the subject, zoom commands to select viewpoints farther from the subject, and/or swipe gestures to select viewpoints rotated about the subject.

In some embodiments, the first image is a color map. In general, there are three categories of color maps used for the visual presentation of information. Nominal, or segmenting, color maps use different hues for different nominal or non-orderable data. Sequential color maps typically use changes in lightness and are commonly applied to the visualization of rankable or orderable data, such as those having low, medium, and high levels. Diverging color maps can be used to split any meaningful numerical data at a mid-point to indicate two categories such as positive and negative, or yes and no. In some embodiments, the first image is a color map having multiple colors. In some embodiments, the red, green, and blue components of the first image are each replaced with their complementary hues in the generation of a false color image.

The terms "first", "second", "third", "fourth", "fifth", and "sixth" when used herein with reference to images, colors, hues, saturations, values, wavelengths, or other elements or properties are simply to more clearly distinguish the two or more elements or properties and are not intended to indicate order.

The terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

What is claimed is:

1. A method of displaying images, the method comprising:
   receiving a first image, wherein the first image comprises an original color and wherein the first image represents a view from a viewpoint;
   acquiring a second image, wherein the second image represents a view from the viewpoint;
   generating, using a computer, a third image by replacing the original color of the first image with a first false color having a first hue;
   producing, using the computer, a fourth image by replacing the original color of the first image with a second false color having a second hue that is complementary to the first hue;
   rendering a fifth image by overlaying the third image and the second image;
   constructing a sixth image by overlaying the fourth image and the second image; and
   alternately displaying the fifth and sixth images.

2. The method of claim 1, wherein the first image has a minimum first image color value and a maximum first image color value, and wherein the first false color and the second false color have a false color value that is within the range between the minimum and maximum first image color values.

3. The method of claim 1, wherein the alternately displaying is performed at a frequency.

4. The method of claim 3, wherein the frequency of the alternately displaying is between 0.1 Hz and 25 Hz.

5. The method of claim 3, further comprising:
   accepting operator input selecting the frequency of the alternately displaying.

6. The method of claim 1, wherein the first and second images each represent views of a biological sample.

7. The method of claim 1, wherein the first image is a fluorescence image, an X-ray image, a positron emission tomography (PET) image, a photon emission computed tomography (SPECT) image, a magnetic resonance imaging (MRI) image, a nuclear magnetic resonance (NMR) image, an ultrasound image, an autoradiography image, an immunohistochemistry image, or a microscopy image.

8. The method of claim 1, wherein the second image is a reflected light image or a tomography image.

9. A method of displaying images, the method comprising:
   receiving a first image, wherein the first image comprises an original color and wherein the first image represents a view from a viewpoint;
   generating, using a computer, a second image by replacing the original color of the first image with a first false color having a first hue;
   producing, using the computer, a third image by replacing the original color of the first image with a second false color having a second hue that is complementary to the first hue; and
   alternately displaying the second and third images.

10. The method of claim 9, wherein the first image has a minimum first image color value and a maximum first image color value, and wherein the first false color and the second false color have a false color value that is within the range between the minimum and maximum first image color values.

11. The method of claim 9, wherein the alternately displaying is performed at a frequency, and wherein the method further comprises:

accepting operator input selecting the frequency of the alternately displaying.

12. The method of claim 9, wherein the first image is a reflected light image, a fluorescence image, an X-ray image, a positron emission tomography (PET) image, a photon emission computed tomography (SPECT) image, a magnetic resonance imaging (MRI) image, a nuclear magnetic resonance (NMR) image, an ultrasound image, an autoradiography image, an immunohistochemistry image, or a microscopy image.

13. The method of claim 9, further comprising:

accepting operator input selecting the viewpoint.

14. A method of displaying images, the method comprising:

receiving a first image, wherein the first image comprises an original color having a first hue and wherein the first image represents a view from a viewpoint;

acquiring a second image, wherein the second image represents a view from the viewpoint;

generating, using a computer, a third image by replacing the original color of the first image with a false color having a second hue that is complementary to the first hue;

rendering a fourth image by overlaying the third image and the second image;

constructing a fifth image by overlaying the first image and the second image; and alternately displaying the fourth and fifth images.

15. The method of claim 14, wherein the first image has a minimum first image color value and a maximum first image color value, and wherein the false color has a false color value that is within the range between the minimum and maximum first image color values.

16. The method of claim 14, wherein the alternately displaying is performed at a frequency.

17. The method of claim 16, wherein the frequency of the alternately displaying is between 0.1 Hz and 25 Hz.

18. The method of claim 16, further comprising:

accepting operator input selecting the frequency of the alternately displaying.

19. The method of claim 14, wherein the first and second images each represent views of a biological sample.

20. The method of claim 14, wherein the first image is a fluorescence image, an X-ray image, a positron emission tomography (PET) image, a photon emission computed tomography (SPECT) image, a magnetic resonance imaging (MRI) image, a nuclear magnetic resonance (NMR) image, an ultrasound image, an autoradiography image, an immunohistochemistry image, or a microscopy image.

* * * * *